(12) United States Patent
Liu et al.

(10) Patent No.: US 10,831,957 B2
(45) Date of Patent: Nov. 10, 2020

(54) SIMULATION SCALING WITH DFT AND NON-DFT

(71) Applicant: Synopsys, Inc., Mountain View, CA (US)

(72) Inventors: Jie Liu, San Jose, CA (US); Victor Moroz, Saratoga, CA (US); Michael C. Shaughnessy-Culver, Napa, CA (US); Stephen Lee Smith, Mountain View, CA (US); Yong-Seog Oh, Pleasanton, CA (US); Pratheep Balasingam, San Jose, CA (US); Terry Sylvan Kam-Chiu Ma, Danville, CA (US)

(73) Assignee: Synopsys, Inc., Mountain View, CA (US)

( * ) Notice: Subject to any disclaimer, the term of this patent is extended or adjusted under 35 U.S.C. 154(b) by 103 days.

(21) Appl. No.: 15/861,605

(22) Filed: Jan. 3, 2018

(65) Prior Publication Data
US 2018/0144076 A1 May 24, 2018

Related U.S. Application Data

(63) Continuation of application No. 14/498,458, filed on Sep. 26, 2014, now Pat. No. 9,881,111.

(60) Provisional application No. 61/889,355, filed on Oct. 10, 2013, provisional application No. 61/883,942, filed on Sep. 27, 2013, provisional application No. 61/883,158, filed on Sep. 26, 2013.

(51) Int. Cl.
| | |
|---|---|
| *G06F 7/60* | (2006.01) |
| *G06F 30/33* | (2020.01) |
| *G06F 17/10* | (2006.01) |
| *G06F 30/20* | (2020.01) |
| *G06F 30/23* | (2020.01) |
| *G06F 30/327* | (2020.01) |
| *G06F 30/367* | (2020.01) |
| *G06F 30/3312* | (2020.01) |

(52) U.S. Cl.
CPC .............. *G06F 30/33* (2020.01); *G06F 17/10* (2013.01); *G06F 30/20* (2020.01); *G06F 30/23* (2020.01); *G06F 30/327* (2020.01); *G06F 30/3312* (2020.01); *G06F 30/367* (2020.01)

(58) Field of Classification Search
CPC .................................................. G06F 17/5022
USPC .......................................................... 703/2
See application file for complete search history.

(56) References Cited

U.S. PATENT DOCUMENTS

| | | |
|---|---|---|
| 5,246,800 A | 9/1993 | Muray |
| 5,472,814 A | 12/1995 | Lin |

(Continued)

FOREIGN PATENT DOCUMENTS

| | | |
|---|---|---|
| WO | 00-72185 A2 | 11/2000 |
| WO | 01-08028 A2 | 2/2001 |
| WO | 02-058158 A2 | 7/2002 |

OTHER PUBLICATIONS

U.S. Appl. No. 14/497,695—Final Office Action dated May 3, 2018, 14 pages.

(Continued)

*Primary Examiner* — Timothy A Mudrick
(74) *Attorney, Agent, or Firm* — Haynes Beffel & Wolfeld LLP; Warren S. Wolfeld; Andrew L. Dunlap

(57) ABSTRACT

Electronic design automation modules for simulate the behavior of structures and materials at multiple simulation scales with different simulation modules.

12 Claims, 11 Drawing Sheets

(56) References Cited

U.S. PATENT DOCUMENTS

| | | | |
|---|---|---|---|
| 5,702,847 | A | 12/1997 | Tarumoto et al. |
| 6,057,063 | A | 5/2000 | Liebmann et al. |
| 6,096,458 | A | 8/2000 | Hibbs |
| 6,685,772 | B2 | 2/2004 | Goddard, III et al. |
| 7,448,022 | B1 | 11/2008 | Ram et al. |
| 7,756,687 | B2 | 7/2010 | Hwang et al. |
| 8,082,130 | B2 | 12/2011 | Guo et al. |
| 8,112,231 | B2 | 2/2012 | Samukawa |
| 8,434,084 | B2 | 4/2013 | Ferdous et al. |
| 8,453,102 | B1 | 5/2013 | Pack et al. |
| 8,454,748 | B2 | 6/2013 | Iwaki et al. |
| 8,555,281 | B1 | 10/2013 | van Dijk et al. |
| 8,572,523 | B2 | 10/2013 | Tuncer et al. |
| 8,626,480 | B2 | 1/2014 | Chang et al. |
| 8,871,670 | B2 | 10/2014 | Seebauer |
| 9,727,675 | B2 | 8/2017 | Liu et al. |
| 9,922,164 | B2 | 3/2018 | Chennamsetty et al. |
| 9,983,979 | B1 | 5/2018 | Dolinsky et al. |
| 2002/0142495 | A1 | 10/2002 | Usujima |
| 2003/0139907 | A1* | 7/2003 | McCarthy .......... G05B 17/02 702/183 |
| 2003/0217341 | A1 | 11/2003 | Rajsuman et al. |
| 2003/0217343 | A1 | 11/2003 | Rajsuman et al. |
| 2004/0063225 | A1 | 4/2004 | Borden et al. |
| 2004/0067355 | A1 | 4/2004 | Yadav et al. |
| 2004/0107056 | A1 | 6/2004 | Doerksen et al. |
| 2005/0170379 | A1 | 8/2005 | Kita et al. |
| 2005/0223633 | A1 | 10/2005 | Sankaranarayanan |
| 2005/0278124 | A1 | 12/2005 | Duffy et al. |
| 2005/0281086 | A1 | 12/2005 | Kobayashi et al. |
| 2006/0038171 | A1 | 2/2006 | Hasumi et al. |
| 2006/0101378 | A1 | 5/2006 | Kennedy et al. |
| 2006/0271301 | A1 | 11/2006 | Takada et al. |
| 2007/0177437 | A1 | 8/2007 | Guo |
| 2007/0185695 | A1* | 8/2007 | Neumann ............ G16C 20/30 703/2 |
| 2007/0265725 | A1 | 11/2007 | Liu et al. |
| 2008/0052646 | A1 | 2/2008 | Tuncer et al. |
| 2008/0147360 | A1 | 6/2008 | Fejes et al. |
| 2009/0032910 | A1 | 2/2009 | Ahn et al. |
| 2010/0052180 | A1 | 3/2010 | Nguyen Hoang et al. |
| 2010/0070938 | A1 | 3/2010 | Wang et al. |
| 2010/0318331 | A1 | 12/2010 | Ritchie |
| 2011/0131017 | A1 | 6/2011 | Cheng et al. |
| 2011/0161361 | A1 | 6/2011 | Csanyi et al. |
| 2011/0231804 | A1 | 9/2011 | Liu et al. |
| 2011/0246998 | A1 | 10/2011 | Vaidya et al. |
| 2011/0313741 | A1 | 12/2011 | Langhoff |
| 2011/0313748 | A1 | 12/2011 | Li |
| 2012/0228615 | A1 | 9/2012 | Uochi |
| 2012/0232685 | A1 | 9/2012 | Wang et al. |
| 2013/0139121 | A1 | 5/2013 | Wu et al. |
| 2014/0180645 | A1 | 6/2014 | Lee et al. |
| 2014/0251204 | A1 | 9/2014 | Najmaei et al. |
| 2015/0088473 | A1 | 3/2015 | Liu et al. |
| 2015/0088481 | A1 | 3/2015 | Liu et al. |
| 2015/0089511 | A1 | 3/2015 | Smith et al. |
| 2015/0120259 | A1 | 4/2015 | Klimeck et al. |
| 2016/0171139 | A1 | 6/2016 | Tago et al. |
| 2016/0335381 | A1 | 11/2016 | Liu et al. |
| 2019/0362042 | A1 | 11/2019 | Oh et al. |

OTHER PUBLICATIONS

U.S. Appl. No. 14/497,695—Response to Office Action dated Jul. 13, 2017 filed Jan. 16, 2018, 19 pages.

U.S. Appl. No. 15/021,655—Office Action dated Apr. 19, 2018, 43 pages.

U.S. Appl. No. 14/497,681—Final Office Action dated May 11, 2018, 19 pages.

PCT/US2014/057637—International Search Report and Written Opinion dated Jan. 5, 2015, 12 pages.

Wang, Yan, "Multiscale Simulations", Georgia Institute of Technology, available at http://www-old.me.gatech.edu/~ywang/CANE/lect05_MultiscaleSims_yanwang.pdf, (dated May 14-16, 2012), 40 pages.

Braunstein, Rubin, et al., "Intrinsic Optical Absorption in Germanium-Silicon Alloys", Physical Review, vol. 109, No. 3, (Feb. 1, 1958), pp. 695-710.

Sant, Saurabh, et al., "Band gap bowing and band offsets in relaxed and strained Si1-xGex alloys by employing a new nonlinear interpolation scheme", published online Jan. 18, 2013, Journal of Applied Physics, vol. 113, pp. 033708-1 through 033708-10.

Uppal, S., et al., "Diffusion of boron in germanium at 800-900° C.", Journal of Applied Physics, vol. 96, No. 3, (Aug. 1, 2004), pp. 1376-1380.

Haddara, Y.M., et al., "Accurate measurements of the intrinsic diffusivities of boron and phosphorus in silicon", Applied Physics Letters, vol. 77, No. 13, (Sep. 25, 2000), pp. 1976-1978.

Uppal, S., et al., "Diffusion of ion-implanted boron in germanium", Journal of Applied Physics, vol. 90, No. 8, (Oct. 2001), 4293-4295.

Stadler, J., et al., "IMD: a Software Package for Molecular Dynamics Studies on Parallel Computers", International Journal of Modren Physics C, vol. 8, No. 5, (Oct. 1997), pp. 1131-1140.

Refson, Keith, "Moldy: a portable molecular dynamics simulation program for serial and parallel computers", Computer Physics Communications, vol. 126, issue 3, (Apr. 11, 2000), pp. 310-329.

Smith, W., et al., "DL_POLY: Application to molecular simulation", Molecular Simulation, vol. 28, Issue 5, (May 5, 2002), pp. 385-471.

Smith, W., and Forester, T.R., "DL_POLY_2.0: A general-purpose parallel molecular dynamics simulation package", Journal of Molecular Graphics, vol. 14, Issue 3, (Jun. 1996), pp. 136-141.

Nieminen, Risto M., "From atomistic simulation towards multiscale modelling of materials", J. Phys.: Condens. Matter, (published Mar. 8, 2002), vol. 14, pp. 2859-2876.

"Simulation of Random Dopant Fluctuation Effects in TCAD Sentaurus", TCAD News, Dec. 2009, Synopsys, Mountain View, CA, USA, 4 pages.

Yu, P.Y., and Cardona, M., "2. Electronic Band Structures", Fundamentals of Semiconductors, Graduate Texts in Physics, 4th ed., Springer-Verlag Berlin Heidelberg, (2010), pp. 17-106.

"ITRS, International Technology Roadmap for Semiconductors, 2012 Update", (2012), available at http://www.itrs.net/Links/2012ITRS/2012Chapters/2012Overview.pdf, 76 pages.

"Sentaurus TCAD" datasheet, Synopsys, Inc., Mountain View, CA USA, May 2012, 4 pages.

"ITRS, 2012 Overall Roadmap Technology Characteristics (ORTC) Tables", International Technology Roadmap for Semiconductors, 2012, availalbe at http://www.itrs.net/Links/2012ITRS/2012Tables/ORTC_2012Tables.xlsm, visited Oct. 14, 2013, 39 pages.

Hansen, Stephen E., "SUPREM-III User's Manual, Version 8628", (Aug. 1986), available from http://www-tcad.stanford.edu/tcad/programs/suprem3man.pdf, visited Oct. 14, 2013, 186 pages.

"Sentaurus Device" datasheet, Synopsys, Inc., Mountain View, CA, USA, Feb. 2007, 8 pages.

Dunham, Scott T., "A Quantitative Model for the Coupled Diffusion of Phosphorus and Point Defects in Silicon", J. Electrochem. Soc., vol. 139, No. 9, (Sep. 1992), pp. 2628-2636.

Skinner, Richard D., editor, "Basic Integrated Circuit Manufacturing", section 2 of "Technology Reference Manual", ICE, Integrated Circuit Engineering, (1993), 112 pages.

Nagel, et al., "Spice (Simulation Program with Integrated Circuit Emphasis)", Memorandum No. ERL-M382, Electronics Research Laboratory, College of engineering, University of California, Berkeley, CA USA, (Apr. 12, 1973), 65 pages.

Quarles, Thomas Linwood, "Analysis of Performance and Convergence Issues for Circuit Simulation", Memorandum No. UCB/ERL M89/42, Electronics Research Laboratory, College of Engineering, University of California, Berkeley, CA USA, (Apr. 1989), 142 pages.

Dunga, Mohan V., et al., "BSIM4.6.0 MOSFET Model—User's Manual", Department of Electrical Engineering and Computer Sciences, University of California, Berkeley, CA USA, 2006, 201 pages.

(56) References Cited

OTHER PUBLICATIONS

Burke, Kieron, and friends, "The ABC of DFT", Department of Chemistry, University of California, Irvine, CA, (Apr. 10, 2007), available at http://chem.ps.uci.edu/~kieron/dft/book/, 104 pages.
Luisier, Mathieu, "Quantum Transport Beyond the Effective Mass Approximation", Diss. ETH No. 17016, 2007, 150 pages.
Taur, Y., "CMOS design near the limit of scaling", IBM J. Res. & Dev., vol. 46, No. 2/3, Mar./May 2002, pp. 213-212.
Luisier, Mathieu, "Quantum Transport for Engineers Lecture 4: Wave Function (WF) formalism and electrostatics", Integrated Systems Laboratory, ETH Zurich (2012), 34 pages.
Kim, Kyoung-Youm and Lee, Byoungho, "Quantum transport modeling in anisotropic semiconductors using Wigner function formulation", Proceedings Conference on Optoelectronic and Microelectronic Materials and Devices, COMMAD 2000. (2000), pp. 4.
Arovas, Daniel "Lecture Notes on Condensed Matter Physics, Chapter 1 Boltzmann Transport", Department of Physics, University of California, San Diego (2010), pp. 46.
Grau-Crespo, R. "Electronic structure and magnetic coupling in FeSbO4: A DFT study using hybrid functionals and GGA+U methods", Physical Review B 73, (2006), pp. 9.
Côté, Michel, "Introduction to DFT+U", International Summer School on Numerical Methods for Correlated Systems in Condensed Matter, Université de Montréal, (2008), pp. 23.
Muramatsu, A., "Quantum Monte Carlo for lattice fermions", in: M.P. Nightingale, C.J. Umriga (Eds.), Proceedings of the NATO Advanced Study Institute on Quantum Monte Carlo Methods in Physics and Chemistry, Kluwer Academic Publishers, (1999), pp. 32.
Gross, E.K.U. and Maitra, N.T., "Introduction to TDDFT", Chapter in Fundamentals of Time-Dependent Density Functional Theory, Springer-Verlag (2012), 58 pages.
Marques, M.A.L. and Gross, E.K.U., "Time-dependent density functional theory," C. Fiolhais, F. Nogueira, M.A.L. Marques (Eds. ), A Primer in Density Functional Theory, Springer Lecture Notes in Physics, vol. 620, Springer (2003), pp. 144-184.
Ryndyk, D.A., "Tight-binding model", Lectures 2006-2007, Dresden University of Technology, (2006-2007), pp. 26-30.
Bank, R.E., "Numerical Methods for Semiconductor Device Simulation", IEEE Transactions on Electron Devices, vol. ED-30, No. 9, (1983), pp. 1031-1041.
Lee, J.F., "Time-Domain Finite-Element Methods", IEEE Transactions on Antenna and Propagation, vol. 45, No. 3, (1997), pp. 430-442.
Eymard, R., "Finite Volume Methods", course at the University of Wroclaw, (2008), manuscript update of the preprint 'n0 97-19 du LATP, UMR 6632, Marseille, (Sep. 1997), Handbook of Numerical Anaylsis P.G. Ciarlet, J.L. Lions, eds. vol. 7, pp. 713-1020.
Chen, X.L., "An advanced 3D boundary element method for characterizations of composite materials", Engineering Analysis with Boundary Elements 29, (2005), pp. 513-523.
Marx, D., "Ab initio molecular dynamics: Theory and Implementation", Modern Methods and Algorithms of Quantum Chemistry, J. Grotendorst (Ed.), John von Neumann Institute for Computing, Julich, NIC Series, vol. 1, (2000), pp. 150.
Kresse, Georg, et al., "VASP the Guide",http://cms_mpi.univie.ac. atNASP, Sep. 9, 2013, Vienna, Austria, pp. 1-203.
PCT/US2014/057707—International Search Report and Wirtten Opinion dated Dec. 29, 2014, 16 pages.
PCT/US2014/057707—International Preliminary report on Patentability, 8 pages.
PCT/US2014/057637—International Preliminary Report on Patentability dated Mar. 29, 2016, 7 pages.
U.S. Appl. No. 14/906,543—Office Action dated Jun. 17, 2016, 26 pages.
PCT/US2014/057840—International Search Report dated Nov. 28, 2014, 9 pages.
U.S. Appl. No. 15/081,735—Office Action dated Jun. 15, 2016, 16 pages.
Saha et al., Technology CAD: Technology Modeling, Device Design and Simulation, 2004 VLSI Design Tutorial, Mubai, India, Jan. 5, 2004, 227 pages.
U.S. Appl. No. 14/497,681—Office Action dated Aug. 25, 2016, 20 pages.
Ayyadi et al., Semiconductor Simulations Using a Coupled Quantum Drift-Diffusion Schrodinger-Poisson Model, Aug. 12, 2004, Vienna University of Technology, pp. 1-19.
Kresse, G., et. al., VASP the Guide (Sep. 9, 2013), pp. 203.
U.S. Appl. No. 15/024,009—Final Office Action dated Nov. 18, 2016, 24 pages.
U.S. Appl. No. 15/081,735—Office Action dated Dec. 13, 2016, 30 pages.
PCT/US2014/057840—International Preliminary Report on Patentability dated Mar. 29, 2016, 5 pages.
U.S. Appl. No. 15/081,735—Response to Office Action dated Jun. 15, 2016 filed Nov. 15, 2016, 18 pages.
PCT/US2014/057803—International Search Report and Written Opinion dated Nov. 28, 2014, 14 pages.
U.S. Appl. No. 15/024,009—Office Action dated Jul. 21, 2016, 24 pages.
U.S. Appl. No. 15/024,009—Response to Office Action dated Jul. 21, 2016 filed Nov. 1, 2016, 38 pages.
U.S. Appl. No. 15/024,009—Preliminary Amendment filed Mar. 22, 2016, 9 pages.
Martin-Bragado et al., "Modeling charged defects, dopant diffusion and activation mechanisms for TCAD simulations using Kinetic Monte Carlos," Nuclear Instruments and Methods in Physics Research Section B: Beam Interactions with Materials and Atoms, 253:1, 18 pages, Dec 2006.
Nagel, Laurence W., "SPICE2: A Computer Program to Simulate Semiconductor Circuits", Memorandum No. UCB/ERL-M520, Electronics Research Laboratory, College of Engineering, University of California, Berkeley, CA USA, (May 9, 1975), 431 pages.
Synopsys, Sentaurus TCAD, Industry-Standard Process and Device Simulators, Datasheet (2012), 4 pages.
Yip, S. (ed.), Handbook of Materials Modeling, 565-588. c 2005 Springer.
U.S. Appl. No. 14/497,681—Response to Office Action dated Aug. 25, 2016 filed Jan. 24, 2017, 10 pages.
U.S. Appl. No. 14/906,543—Response to Office Action dated Jun. 17, 2016 filed Dec. 19, 2016, 23 pages.
U.S. Appl. No. 14/906,543—Final Office Action dated Feb. 10, 2017, 16 pages.
U.S. Appl. No. 14/906,543—Preliminary Amendment dated Jan. 20, 2016, 8 pages.
U.S. Appl. No. 15/081,735—Response to Office Action dated Dec. 13, 2016, filed Mar. 13, 2017, 10 pages.
Lee et al., "Area and Volume Measurements of Objects with Irregular Shapes Using Multiple Silhouettes," Optical Engineering 45(2), Feb. 2006, 11 pages.
Keneti, et al., "Determination of Volume and Centroid of Irregular Blocks by a Simplex Integration Approach for Use in Discontinuous Numerical Methods," Geomechanics and Geoengineering: An International Journal, vol. 3, No. 1, Mar. 2008, pp. 79-84.
U.S. Appl. No. 15/081,735—Notice of Allowance dated Mar. 29, 2017, 17 pages.
U.S. Appl. No. 14/497,681—Final Office Action dated May 3, 2017, 28 pages.
Isik, A., "Molecular Dynamics Simulation of Silicon Using Empirical Tight-Binding Method," Massachusetts Institute of Technology, Jan. 1992, 89 pages.
Miloszewski, J., "Simulations of Semiconductor Laser Using Nonequilibrium Green's Functions Method," University of Waterloo, 2012, 129 pages.
U.S. Appl. No. 15/024,009—Response to Final Office Action dated Nov. 18, 2016 filed Mar. 20, 2017, 24 pages.
Jegert, et al. "Role of Defect Relaxation for Trap-Assisted Tunneling in High-k Thin Films: A First-Principles Kinetic Monte Carlo Study" Physical Review B 85.4 (2012), 8 pages.
U.S. Appl. No. 14/497,695—Office Action dated Jul. 13, 2017, 26 pages.

(56) References Cited

OTHER PUBLICATIONS

U.S. Appl. No. 14/498,492—Notice of Allowance dated Aug. 14, 2017, 28 pages.
Clark, "Quantum Mechanics: Density Functional Theory and Practical Application to Alloys." Introduction to Compter Simulation (2010), 51 pages.
U.S. Appl. No. 14/906,543—Response to Final Office Action dated Feb. 10, 2017 filed Jun. 23, 2017, 15 pages.
U.S. Appl. No. 14/906,543—Advisory Action dated Aug. 2, 2017, 4 pages.
U.S. Appl. No. 14/498,458—Notice of Allowance dated Sep. 7, 2017, 29 pages.
U.S. Appl. No. 15/669,722—Office Action dated Oct. 6, 2017, 30 pages.
U.S. Appl. No. 14/497,681—Response to Final Office Action dated May 3, 2017 filed Nov. 3, 2017, 13 pages.
U.S. Appl. No. 14/497,681—Office Action dated Dec. 20, 2017, 25 pages.
U.S. Appl. No. 15/669,722—Notice of Allowance dated Mar. 7, 2018, 5 pages.
U.S. Appl. No. 15/669,722—Response to Office Action dated Oct. 6, 2017 filed Jan. 10, 2018, 3 pages.
U.S. Appl. No. 14/497,681—Response to Office Action dated Dec. 20, 2017 filed Mar. 20, 2018, 11 pages.
Bortolossi, "3D Finite Element Drift-Diffusion Simulation of Semiconductor Devices," Jul. 25, 2014, Politecnico di Milano, 132 pages.
Capelle, "A Bird's-Eye View of Density-Functional Theory", Departarnento de Fisica e Infoimatica Instituto de Fisica de Sao Carlos, Universidade de Sao Paulo, Caixa Postal 369, Sao Carlos, 13560-970 SP, Brazil, arXiv:cond-mat/0211443v5 [cond-mat.mtrl-sci], Nov. 18, 2006, pp. 1- 69.
Pomorski et al., "Capacitance, induced charges, and bound states of biased carbon nanotube systems," 2004, Physical Review B 69.11 , 115418, pp. 1-16.
Sverdlov et al., "Current Transport Models for Nanoscale Semiconductor Devices," 2008, Materials Science and Engineering: R: Reports 58.6, pp. 228-270.
Taylor et al., "Ab initio modeling of quantum transport properties of molecular electronic devices", 2001, Physical Review B 63.24, 245407, pp. 1-13.
U.S. Appl. No. 14/497,681—Advisory Action dated Aug. 3, 2018, 7 pages.
U.S. Appl. No. 14/497,681—Final Office Action dated Feb. 7, 2019, 23 pages.
U.S. Appl. No. 14/497,681—Notice of Allowance dated Jul. 25, 2019, 22 pages.
U.S. Appl. No. 14/497,681—Office Action dated Sep. 5, 2018, 22 pages.
U.S. Appl. No. 14/497,695—Advisory Action dated Aug. 23, 2018, 3 pages.
U.S. Appl. No. 14/497,695—Notice of Allowance dated May 13, 2019, 10 pages.
U.S. Appl. No. 14/497,695—Notice of Allowance dated Aug. 14, 2019, 11 pages.
U.S. Appl. No. 14/497,695—Office Action dated Sep. 21, 2018, 18 pages.
U.S. Appl. No. 15/021,655—Notice of Allowance dated May 1, 2019, 12 pages.
U.S. Appl. No. 15/021,655—Notice of Allowance dated Nov. 7, 2018, 13 pages.
U.S. Appl. No. 15/224,165—Advisory Action dated Jun. 27, 2019, 4 pages.
U.S. Appl. No. 15/224,165—Final Office Action dated Feb. 6, 2019, 14 pages.
U.S. Appl. No. 15/224,165—Final Office Action dated Sep. 20, 2019, 22 pages.
U.S. Appl. No. 15/224,165—Office Action dated Aug. 7, 2018, 47 pages.
Zhu et al., "Time-dependent quantum transport: Direct analysis in the time domain," 2005, Physical Review B 71.7: 075317, pp. 1-10.

* cited by examiner

SIMULATION SCALING WITH DFT AND NON-DFT

REFERENCE TO RELATED APPLICATIONS

This application is a continuation of U.S. application Ser. No. 14/498,458, filed Sep. 26, 2014, entitled "SIMULATION SCALING WITH DFT AND NON-DFT", which claims the benefit U.S. Provisional Application No. 61/883,158, filed Sep. 26, 2013, entitled "CONNECTING FIRST-PRINCIPLES CALCULATIONS WITH TRANSISTOR CHARACTERIZATION", U.S. Provisional Application No. 61/883,942, filed Sep. 27, 2013, entitled "CONNECTING FIRST-PRINCIPLES CALCULATIONS WITH TRANSISTOR CHARACTERIZATION", and U.S. Provisional Application No. 61/889,355, filed Oct. 10, 2013, entitled "Automated, Adaptive, Multi-scale Technology Computer Aided Design Simulation Tools". All the above applications are incorporated herein by reference in their entirety.

The following patent applications are incorporated by reference herein: International Application No. PCT/US2014/057840, titled "PARAMETER EXTRACTION OF DFT" filed Sep. 26, 2014; and U.S. application Ser. No. 14/498,492, titled "ITERATIVE SIMULATION WITH DFT AND NON-DFT" filed Sep. 26, 2014.

BACKGROUND

Field of the Invention

The present invention relates to electronic design automation, and modules for simulating the behavior of structures and materials at multiple simulation scales with different simulation modules.

SUMMARY

One aspect of the technology is an EDA tool comprising a data processor; and storage configured to provide computer program instructions to the processor.

The storage includes a controller module causing a plurality of simulation modules to perform an EDA simulation at a plurality of different simulation scales. The plurality of simulation modules include a first set of one or more ab initio simulation modules simulating a first volume with a first boundary, and a second set of one of more non-ab initio simulation modules simulating a second volume with a second boundary. The second volume is larger than the first volume.

The controller module causes, responsive to a simulated volume occupied by a nonzero part of a simulated property being a larger percentage of the second volume than the first volume, switching from the second set of one or more non-ab initio simulation modules to the first set of one of more ab initio simulation modules.

In one embodiment, the simulated property as simulated by the first set of one or more ab initio simulation modules is equal at the first boundary to an asymptotic value of the simulated property.

In one embodiment, the simulated property as simulated by the second set of one or more ab initio simulation modules is equal at the second boundary to an asymptotic value of the simulated property.

In one embodiment, the simulated volume fits within the first volume.

In one embodiment, the first set of one or more simulation modules includes a density functional theory module, and the second set of one or more simulation modules excludes the density functional theory module.

Another aspect of the technology is a computer-implemented method comprising:

causing a plurality of simulation modules to perform an EDA simulation at a plurality of different simulation scales, the plurality of simulation modules including:

a first set of one or more ab initio simulation modules simulating a first volume with a first boundary; and a second set of one of more non-ab initio simulation modules simulating a second volume with a second boundary, the second volume larger than the first volume; and causing, responsive to a simulated volume occupied by a nonzero part of a simulated property being a larger percentage of the second volume than the first volume, switching from the second set of one or more non-ab initio simulation modules to the first set of one of more ab initio simulation modules.

Various embodiments are disclosed herein.

One aspect of the technology is an EDA tool comprising a data processor; and storage configured to provide computer program instructions to the processor.

The storage includes a controller module causing a plurality of simulation modules to perform an EDA simulation at a plurality of different simulation scales. The plurality of simulation modules includes a first set of one or more ab initio simulation modules of a first volume with a first boundary; and a second set of one of more non-ab initio simulation modules of a second volume with a second boundary, the second volume larger than the first volume.

The controller module causes the first set of one or more ab initio simulation modules to perform the EDA simulation of a simulated property, and depending on whether a nonzero magnitude of an error of the simulated property exceeds an error threshold, the controller module causes one of: (i) switching from the first set of one or more ab initio simulation modules to the second set of one of more non-ab initio simulation modules, and (ii) remaining with the first set of one or more ab initio simulation modules despite the error.

In one embodiment, the error is a nonzero difference between:

(i) the simulated property at the first boundary simulated by the first set of one or more ab initio simulation modules, and (ii) an asymptotic value of the simulated property beyond the first boundary.

In one embodiment, the asymptotic value is obliquely asymptotic.

In one embodiment, the asymptotic value is horizontally asymptotic.

In one embodiment, the asymptotic value is vertically asymptotic.

In one embodiment, the first set of one or more simulation modules includes a density functional theory module, and the second set of one or more simulation modules excludes the density functional theory module.

Another aspect of the technology is a computer-implemented method comprising:

causing a plurality of simulation modules to perform an EDA simulation at a plurality of different simulation scales, the plurality of simulation modules including:

a first set of one or more ab initio simulation modules of a first volume with a first boundary; and a second set of one of more non-ab initio simulation modules of a second volume with a second boundary, the second volume larger than the first volume; and causing the first set of one or more ab initio simulation modules to perform the EDA simulation of a simulated property, and depending on whether a nonzero magnitude of an error of the simulated property exceeds an error threshold, causing one of: (i) switching from the first set of one or more ab initio simulation modules to the second set of one of more non-ab initio simulation modules, and (ii) remaining with the first set of one or more ab initio simulation modules despite the error.

Various embodiments are disclosed herein.

Other aspects and advantages of the present technology can be seen on review of the drawings, the detailed description and the claims, which follow.

DETAILED DESCRIPTION

Figure 1:
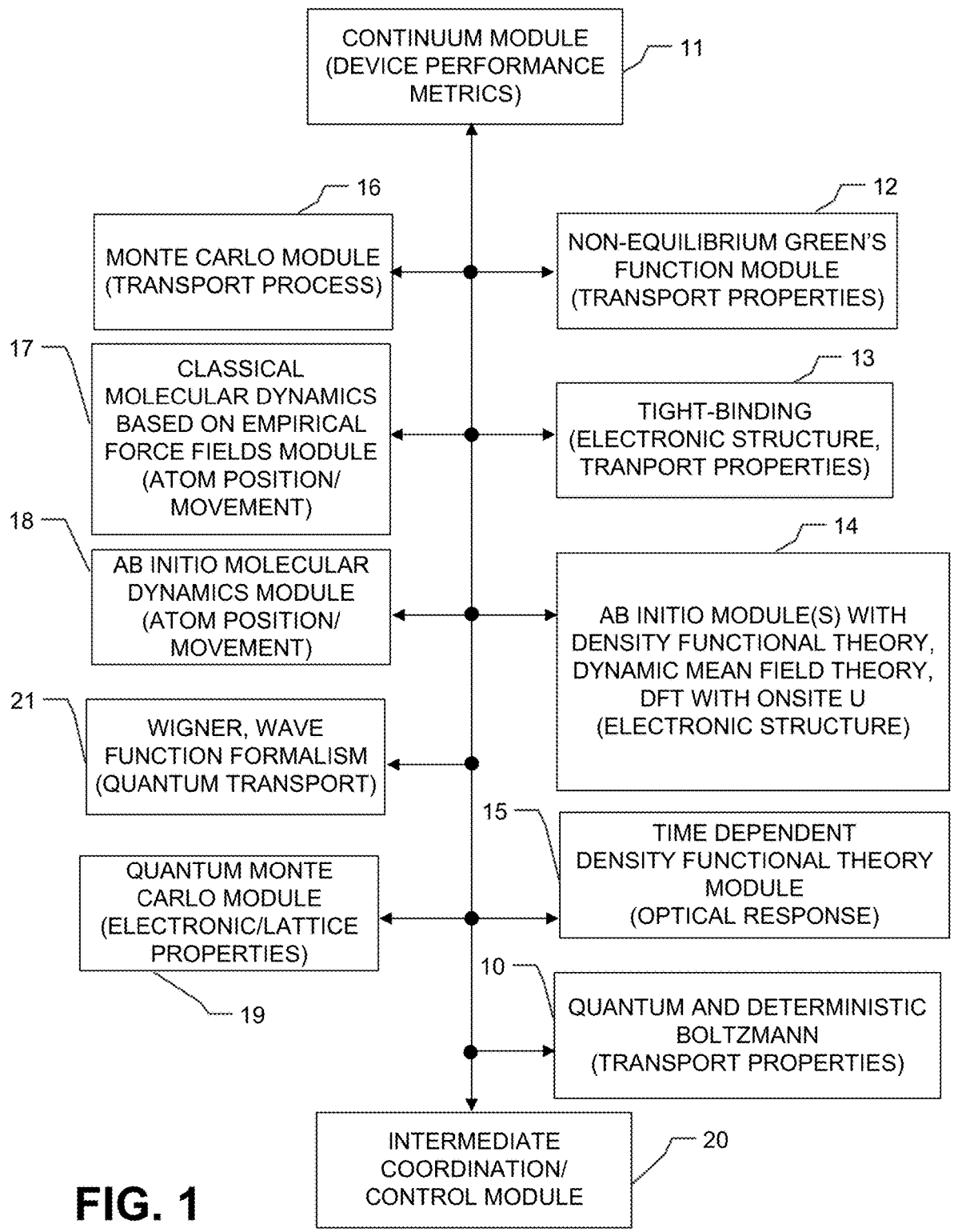
FIG. 1 is a block diagram of various simulation modules at multiple simulation scales coupled together and using output of one module as input for another module, and automatically executing another module at the same simulation scale or different simulation scale to improve inaccurate input (such as missing input).

A detailed description of embodiments of the present invention is provided with reference to the Figures.

As processing power increases sufficiently, scaling tools can simulate transistor behavior at increasingly granular levels, even at the atomic level. A trade-off exists among granularity of the simulation, and required computation resources. For example, fine granularity increases required computation resources, and so tends to have reduced simulation volume. In another example, coarse granularity reduces computation resources, and so tends to have enlarged simulation volume.

There are many levels of how detailed the physical model can be. Typically, simpler models can handle larger examples whereas more sophisticated models typically can only handle a smaller subset of such examples within comparable computation time. For example, so-called compact transistor models like BSIM represent a transistor as several empirical formulas that can be calculated within milliseconds. This enables such compact models to be used in characterizing large circuits that contain thousands of transistors. A more sophisticated Technology Computer-Aided Design (TCAD) model represents transistor as hundreds of thousands of interconnected points that are scattered throughout different parts of the transistor. Several key Partial Differential Equations (PDEs) are solved on these interconnected points and determine distribution of the charges and electrostatic potential throughout the transistor, as well as the charge transport between the terminals. The TCAD model typically handles a handful of transistors (say, from 1 to 5) in the same timeframe as the compact model handles thousands of transistors in a circuit. The upside for the TCAD model is that it can predict transistor behavior based on the known material properties, whereas the compact model typically needs to be calibrated either to TCAD model or to experiments. Yet another modeling level is Density Functional Theory (DFT), which typically cannot represent an entire transistor, but represents a small part of it, considering each atom separately and how the atoms are connected to each other. A collection of atoms of the order of 100 hundred, which is less than one percent of the atoms in a transistor, can be characterized by DFT in the same timeframe as TCAD handles a few transistors and the compact model handles a thousand transistors. The DFT model can predict material properties based on the atomic properties, and therefore can provide the input for the TCAD model to characterize the transistor. So, there is a hierarchy of modeling approaches, including DFT (sometimes referred to as "first principles" approach), TCAD, and compact models. The tools in this hierarchy are applied sequentially, going from detailed physics/small structure towards the simpler physics and larger size, and usually this works fine. However, there are cases where this hierarchical approach fails, and there are more such cases as the transistor scaling continues. There are some characteristics that typically can be obtained only with large enough structure size. For example, typically one can only get accurate electric field distribution and the current crowding/filamentation effects on transistor scale, i.e. a TCAD level model. Such characteristics can affect the inter-atomic bonds and the band structure, and therefore alter results of DFT analysis that cannot calculate such characteristics on the scale it can handle. The present approach bridges this gap.

FIG. 1 is a block diagram of various simulation modules at multiple simulation scales coupled together and using output of one module as input for another module, and automatically executing another module at the same simulation scale or different simulation scale to improve inaccurate input (such as missing input). Details of the blocks are discussed in U.S. Provisional Applications 61/883,158 filed Sep. 26, 2013; and U.S. Application No. 61/883,942 filed Sep. 27, 2013; and U.S. Application No. 61/889,355 filed Oct. 10, 2013, incorporated herein by reference.

This technique adaptively combines multiple simulation and design modules and methodologies, in order to offer automated, self-adaptive, and multi-scale simulation capabilities of various physical processes in the fabrication and operation of integrated circuit devices. The modules can include several hierarchical simulation modules, each of which focuses on the physical processes in one particular spatial scale. The modules can communicate in one direction, or back-and-forth with each other via parameter extraction in an automated and self-adaptive way.

The multiple modules can have one or more of multiple benefits. Firstly, multiple modules offer systematic and comprehensive simulation capabilities of the physical processes in multiple spatial scales. While the existing simulation methodologies focus on the physical processes in one particular spatial scale, the modules include them as internal modules or at least modules communicating via an intermediate module, and offer systematic simulation functionalities in multiple spatial scales. Secondly, the modules help reducing the cost of experiment and testing by including ab initio simulations modules as the internal modules, or as external modules in communication via an intermediate module, which can offer valuable physical insights and replace empirical experiments and calibrations. Thirdly, the modules can significantly reduce computational time and consumption of computational resources, by replacing some computationally expensive calculations via parameter extraction. Fourthly, the modules are able to control the simulation automatically and self-adaptively, hence minimizing the needs of human control and intervention.

Without the modules, one needs to be an expert of many sophisticated simulation modules and methodologies, to perform simulations of physical processes which span multiple spatial scales. The simulations performed in this fashion are functionality limited, physical expertise demanding, computationally expensive, human time intensive, and error prone. The modules are dedicated to solve these problems.

Example modules shown in FIG. 1 include: quantum Monte Carlo (QMC) 19; time-dependent density functional theory (TD-DFT) 15; density functional theory (DFT), DFT with on-site U (DFT+U) 14, and dynamic mean field theory (DMFT) 14; ab initio molecular dynamics (AIMD) 18; tight binding (TB) 13; classical molecular dynamics (MD) 17; Monte Carlo (MC) 16; non-equilibrium Green's function (NEGF) 12; Wigner and wave function formalism quantum transport 21; quantum and deterministic Boltzmann transport 10; and various continuum simulation modules and methodologies (continuum), etc.

Example information flows between the different modules, are follows:

The QMC module solves the many-body physics problems. The electronic structure and lattice structure properties calculated from QMC are the output of the modules. Since the mean field theory methodologies DFT and TD-DFT sometimes give imprecise results (e.g. band structure, band gap, etc.), the QMC module can verify the results. Similarly, the QMC module can benchmark the MD, AIMD, TB, MC, NEGF, and continuum modules, to simulate the atomic movement, transport properties, and various device performance metrics.

The TD-DFT module solves the time dependent Schrodinger equation. The various optical response properties of materials and the atomic movement under external excitation can be obtained from the TD-DFT module. Since the DFT may not account for electronic excitation, the TD-DFT module can benchmark DFT results when the electronic excitation cannot be ignored. The inter-atomic force computed from TD-DFT is used in the AIMD and MD modules to obtain the atomic trajectory. The optical response related parameters used in the MC, NEGF, and continuum modules are computed from the TD-DFT module.

The DFT module can include not only the DFT modules based on mean field theory and single particle approximation, but also strong correlation simulation algorithms like DMFT and DFT+U. The DFT module can generate the electronic structure. The inter-atomic forces computed in the DFT module is used to calculate the atomic movement in the AIMD module. The energy calculated in the DFT module is used to generate empirical force fields, which can be used in the MD module, by using methods like parameter fitting and/or optimization algorithms. The various phenomenological parameters in the TB, MC, and continuum modules are calibrated and optimized using batch calculations in the DFT module. The Hamiltonian and overlap matrices in the NEGF module can be obtained from the DFT module.

DFT is an example of a class of approaches known as "ab initio" or "first principles" approaches. Such approaches require minimal empirical input to generate accurate ground state total energies for arbitrary configurations of atoms. These approaches make use of fundamental quantum mechanical equations, and require very little in the way of externally-supplied materials parameters. This capability makes these methods well-suited to investigating new materials and to providing highly detailed physical insight into material properties and processes, but also renders them extremely computation intensive. As such, a task control system can control a multi-scale simulation project in which any of the ab initio approaches is used in combination with less computation intensive approaches such as 2D Schrodinger and TCAD. As used herein, an "ab initio" or "first principles" analysis approach or module is an approach or module that develops its results at least in part by solving Schrodinger's equation based on positions and types of atoms. Other example first principles approaches that can be used herein include EPM (Empirical Pseudo-potential Method) modules, and ETB (Empirical Tight Binding) modules, and combinations of approaches.

The TB module is based on phenomenological expressions of various physical quantities. It can be used to compute electronic and transport properties. The inter-atomic forces calculated in the TB module can be used to generate the force field in the MD module. The TB description of the target system (e.g. Hamiltonian) is used in the MC, NEGF, and continuum models to obtain the physical properties pertaining to electron transport and device process.

The NEGF module computes the transport properties, which are the output of the modules. The NEGF module can simulate not only transport with scattering, but also ballistic transport. So it can be used to benchmark the continuum module, especially when the transport is largely ballistic. Also, the physical properties (local density of states, transmission, mean free path, etc.) obtained from the NEGF module can offer valuable insights in the ultra-scaled devices. NEGF iterates between (i) the Poisson equation to get a 3D potential profile U, and (ii) the NEGF transport equation to get a density matrix rho. NEGF also generates the following distributions: electron charge density, hole charge density, electron velocity, hole velocity, electrostatic potential, current (product of respective charge density and charge velocity).

The MC module includes, but is not limited to, device MC, kinetic MC, and lattice kinetic MC. The device operation physics and fabrication process are the output of the MC module. The MC module can take the output from other modules as input. For example, the energy dumped by the DFT module can be used to estimate the activation energy in the MC module to evaluate the atomic migration probability. The MC module is capable of simulating many physical processes, e.g. dopant diffusion during process, electron transport, atom migration, etc.

The quantum and deterministic Boltzmann module relies on the Boltzmann equation for calculation of transport properties.

The Wigner and wave function formalism module calculates quantum transport properties.

The continuum module accepts output of the other modules and use them as input, to calculate various device performance metrics, like charge distribution, current-voltage curve, etc. The continuum module includes various numerical algorithms like finite element method, finite volume method, finite difference time domain method, boundary element method, etc. The continuum module can be considered an intermediate module that communicates between different modules.

The coordination module coordinates the other modules. If a particular module has missing input, the coordination module executes another module to provide the missing input. If a particular simulation scale is not specified in the execution instruction, the coordination module determines the appropriate scales to run. The proposed modules receive target simulation quantities via a user interface, and instruct the coordination module to start the simulation. After receiving the simulation instructions, the coordination module decides which functional block(s) should be called to perform these simulation tasks. To accomplish the entire user request, the functional blocks of the proposed module may be called many times adaptively and iteratively by the coordination module. The communication of information (like parameter request and extraction) between/among the functional blocks is controlled by the coordination module. The coordination module can be considered an intermediate module that coordinates different modules.

A particular simulation module can be integrated into a suite of multiple simulation modules. Alternatively, intermediate modules can process output from discrete simulation modules for use as input by each other.

In one example division of different simulation scales, a complete semiconductor device scale includes SPICE and other continuum modules. The ab initio simulation scale can include AIMD, DFT, DMFT, DFT+U, TD-DFT, and QMC. The intermediate simulation scale can include MC, NEGF, MD, and TB. Drift-diffusion can be a large scale. Different simulations scales can be viewed also as a continuum of scales, with finer gradations of scale, such that any pair of tools can have overlapping or non-overlapping simulation volumes.

Figure 2:
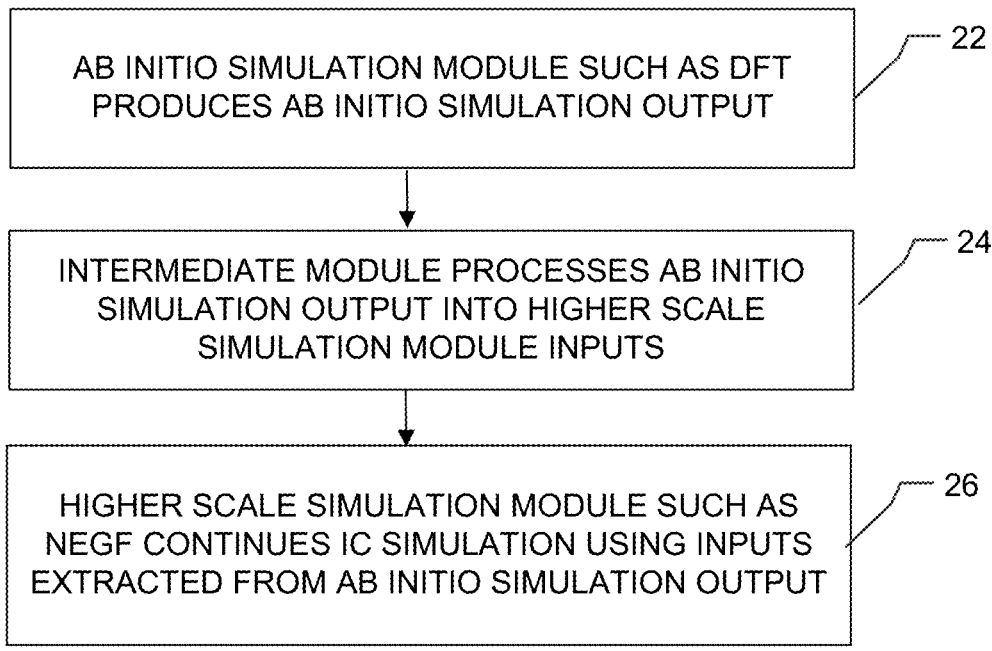
FIG. 2 is an example block diagram of simulation modules at multiple simulation scales coupled together via an intermediate module using output of an ab initio simulation module as input for a higher scale simulation module

FIG. 2 is an example block diagram of simulation modules at multiple simulation scales coupled together via an intermediate module using output of an ab initio simulation module as input for a higher scale simulation tool. To take advantage of the accuracy of more granular simulation, and the lowered computation intensity of less granular simulation, parameters are passed between multiple levels of simulation.

One such combination uses DFT to develop inputs for NEGF, and uses NEGF to simulate larger volumes than would be possible with DFT alone.

At 22, results are produced from an ab initio simulation module such as DFT. At 24, results are processed into higher simulation scale input. Processing can be as minimal as passing a parameter, or performing multiple operations to extract data. At 26, the simulation is continued using the results from the ab initio simulation module as input of an intermediate scale simulation module such as NEGF.

DFT receives input such as types and coordinates of all atoms that comprise the structure, coordinates of additional electrons and holes, and boundary conditions of electrostatic potential. DFT generates as output, band structure, bandgap Eg, Young modulus E, Poisson ratio v, hole and electron effective mass m*, permittivity, into larger scale simulations. For example, NEGF can directly use this output as the Hamiltonian. TCAD can adjust the mobility with this output. SPICE parameters can be adjusted with this output.

One DFT embodiment performs the simulation with only internal fields or potential barriers. Another DFT embodiment performs the simulation with an external field output from NEGF or other higher scale modules.

The scheme can offer one or more of multiple benefits. (1) It enables the calculation of large systems which are too computationally expensive for the ab initio simulation modules. (2) It enables simulation of the physical process whose duration is too long for the ab initio simulation modules. (3) It enables batch simulations of a large number of systems which are too computational resource consuming for the ab initio simulation modules. (4) It improves the calculation precision of the phenomenological simulation modules and methodologies by adaptively extracting parameters from the comparatively more accurate ab initio simulation modules. (5) It offers automated and self-adaptive calculation scheme, which minimizes needs of human intervention and maximizes productivity of simulation and design.

Without the scheme, one typically needs to perform the parameter extraction process based on prior simulation experience and intuition, which are not only human time intensive but also error prone. This scheme solves this problem, by automating the parameter extraction from the ab initio simulation modules with an intermediate module, and using the extracted parameters in the phenomenological simulation modules.

The ab initio scale simulation modules and methodologies mentioned above can include, but are not limited to, the following modules: quantum Monte Carlo (QMC), time dependent density functional theory (TD-DFT), density functional theory (DFT), and ab initio molecular dynamics (AIMD), etc.

The intermediate scale phenomenological simulation modules and methodologies" mentioned above include, but not limited to, the following modules: classical molecular dynamics (MD), Monte Carlo (MC), tight-binding (TB), non-equilibrium Green's function (NEGF), and continuum simulation methods. Different simulations scales can be viewed also as a continuum of scales, with finer gradations of scale, such that any pair of tools can have overlapping or non-overlapping simulation volumes.

The intermediate module extracts parameters from ab initio density functional theory (DFT) simulations. The extracted parameters can be used as the inputs of other modules (e.g. Monte Carlo), to facilitate multi-scale simulations. Example applications of the DFT intermediate tool output are: capacitance calculator, circuit simulator for simulation operation of a circuit of devices, device simulator for computing current-voltage in one device or combination of devices, device simulator based on the solution of partial differential equations, device simulator based on the solution of the Boltzmann transport equation, device simulator based on quantum transport, and device simulator for the simulation of magnetic based devices.

Multi-scale simulation assists downscaling integrated circuit semiconductor devices and exploration of novel materials. Downscaling makes the quantum mechanical effects more important. The new modules help understand new materials' properties and help improve the device design. Users can simulate the devices by combining the ab initio quantum mechanical simulations from first-principles.

One of the most mature and widely-applied ab initio algorithms is the density functional theory (DFT). Simulation modules, such as DFT modules, can be internal to the EDA tool, or an external module by a third party. Examples of DFT tools are VASP, SIESTA, Quantum Espresso, OpenMX, etc.

The physical semiconductor quantities extracted from DFT discussed below in more detail include: bandgap (direct and indirect), effective mass scalar, effective mass tensor, non-parabolicity, and N-band k.p model parameters (such as Luttinger parameters). Although the example below discusses 6-band k.p model Luttinger parameters, other embodiments are directed to various numbers of bands (e.g., 2, 6, 8, 20, etc.). Such preceding parameters can be calculated in different directions such as x, y, and z due to anisotropic behavior. These quantities can be used as the input parameters of other tools.

To extract the bandgap, the intermediate module relies on input of multiple k points, such as k1 (k1x, k1y, k1z) and k2 (k2x, k2y, k2z). Here, k1 specifies the conduction band maximum (CBM) location, and k2 specifies the valence band minimum (VBM) location.

The intermediate module parses the DFT output data, to locate these two k points in the DFT data. Using the Fermi level, intermediate module will automatically determine from which band the eigenvalues E(k1) and E(k2) are extracted. Finally, the result of E(k2)−E(k1) is used as the bandgap value.

The intermediate module can perform data interpolation. Alternatively, it parses DFT data and directly locates E(k1) and E(k2). The two k points can be specified when performing the DFT calculations, such that E(k1) and E(k2) are explicitly contained in the DFT data.

To extract the effective mass tensor, the intermediate module uses three quantities: the band label (which band to compute effective mass tensor), the band structure valley location ko(kox, koy, koz) in the Brillouin zone, and the cutoff value kcut.

Then, the intermediate module performs the extraction calculations. The intermediate module parses the DFT output data and chooses all k points k(kx, ky, kz) which can satisfy $$\sqrt{(k_x-k_{ox})^2+(k_y-k_{oy})^2+(k_z-k_{oz})^2} < k_{cut}$$

Then, using the band label specified, the eigenvalues E(k), including E(ko), corresponding to the chosen k points in the target band are read out from DFT data.

Then, the effective mass tensor mij (i, j=x, y, z) extraction is performed based on the Taylor expansion of the E(k) relation near ko $$E(k) = E(k_0) + \frac{\hbar^2}{2} m_{ij}^{-1} (k_i - k_{oi})(k_j - k_{oj}) + O(|\Delta k|^2)$$

To obtain the numerical values of the effective mass tensor, which has multiple (e.g., six) independent components due to symmetry mij=mji, the linear algebraic equations A X=B is formulated and solved, where A is an n×6 matrix; B and X are 6×1 matrices; and n is the number of chosen k points. The solution of the A X=B is based on least square solution algorithm. The effective mass tensor matrix inversion is calculated.

Therefore, appropriate DFT data such as the kcut value are provided to intermediate module, such that there are sufficient (e.g., 6) linearly independent equations in A X=B. Otherwise, the extraction can crash or give unphysical results.

Also, kcut can be set as an appropriate value. If small enough, all chosen (kx, ky, kz) points are in the parabolic region near (kox, koy, koz). Secondly, if kcut is large enough, the difference E(k)−E(ko) is large enough to ensure extraction accuracy. Although an example kcut=0.01 can be used, kcut is a material-specific parameter to be customized.

To extract the effective mass scalar, the intermediate module uses three inputs: the band label (which band to compute effective mass scalar), the band structure valley location ko(kox, koy, koz) in the Brillouin zone, and another k point kp(kpx, kpy, kpz) near ko.

The intermediate module parses the DFT data and find out the eigenvalues E(kp) and E(ko) in the specified band. Then, using the Taylor expansion of the E(k) relation at ko $$E(k_p) = E(k_0) + \frac{\hbar^2}{2m} |k_p - k_o|^2 + O(|\Delta k|^2)$$

the effective mass scalar m along the direction kp–ko can be computed.

Similar to the effective mass tensor extraction, the |kp–ko| can be small enough such kp that is still in the parabolic region of the valley. And it can be large enough such that the difference E(kp)−E(ko) is large enough to ensure extraction accuracy.

To extract the non-parabolicity parameter α, the intermediate module relies on multiple inputs: the band label (which band to compute effective mass scalar), the band structure valley location ko(kox, koy, koz) in the Brillouin zone, a k point kp(kpx, kpy, kpz) in the parabolic region near ko, and a k point kn(knx, kny, knz) in the non-parabolic region far away from ko.

To extract non-parabolicity, in the first step, the effective mass scalar m along the direction kp–ko is computed as described. Using the value of m, $$E_p(k_n) = E(k_0) + \frac{\hbar^2}{2m} |k_n - k_o|^2$$

is computed to obtain the eigenvalue at kn if the band structure were parabolic. Actually the band structure is non-parabolic at kn, so in the second step, using $$E(kn) = \frac{1}{2\alpha}\left[-1 + \sqrt{1 + 4[E_p(kn) - E(ko)\alpha]}\right] + E(ko)$$

the non-parabolicity parameter α is computed.

The choice of kp follows the principles introduced in effective mass scalar extraction. The choice kn can be pre-specified or up to the user, provided that kn is in the non-parabolic region.

To extract the k.p model parameters, the user or intermediate module provides two inputs to the intermediate module: the location of the band structure valley ko(kox, koy, koz) in the Brillouin zone, and the cutoff value kcut.

The intermediate module extracts the k.p model parameters in multiple steps. In the first step, it parses the DFT data and select the k points k(kx, ky, kz) whose distances to ko are smaller than kcut. Also, the corresponding eigenvalues EDFT(k) in the highest six valence bands are read from DFT data.

In the second step, the initial guess of the model parameters (γ1, γ2, γ3, and Δso) is used to generate the 6×6 Hamiltonian matrix $$H = \begin{bmatrix} P+Q & -S & R & 0 & -S/\sqrt{2} & \sqrt{2}R \\ & P-Q & 0 & R & -\sqrt{2}Q & \sqrt{3/2}S \\ & & P-Q & S & \sqrt{3/2}S^* & \sqrt{2}Q \\ & & & P+Q & -\sqrt{2}R^* & -S^*/\sqrt{2} \\ & & & & P+\Delta so & 0 \\ & & & & & P+\Delta so \end{bmatrix}$$

where $$\begin{cases} P = \frac{\hbar^2}{2m_e}\gamma_1(k_x^2 + k_y^2 + k_z^2) \\ Q = \frac{\hbar^2}{2m_e}\gamma_2(k_x^2 + k_y^2 + k_z^2) \\ R = \frac{\hbar^2}{2m_e}\sqrt{3}[-\gamma_2(k_x^2 - k_y^2) + 2i\gamma_3 k_x k_y] \\ S = \frac{\hbar^2}{2m_e}2\sqrt{3}(k_x - ik_y)k_z \end{cases}$$

according to the k.p theory. Here, me is the electron mass; γ1, γ2, γ3 and are the Luttinger parameters; and Δso is the spin-orbit split-off energy. Then, the eigenvalue problem H(k)X(k)=EBKP(k)X(k)

is solved, using the ZGEEV subroutine as implemented in LAPACK package, to obtain the eigenvalues (e.g., 6) for each selected k point.

In the third step, the difference between the EDFT(k) and the EBKP(k) is evaluated using the cost function, which is defined as $$c = \sqrt{\frac{1}{N_k}\sum_k |E_{BKP}(k) - E_{DFT}(k)|^2}$$

where Nk is the number of selected k points in the extraction. The cost function describes how much the guessed model parameters (γ1, γ2, γ3 and Δso) deviate from the DFT data.

In the fourth step, the cost function is iteratively reduced, by using the simplex optimization algorithm to optimize the model parameters (γ1, γ2, γ3 and Δso). In the iterative optimization of the model parameters, the second and third steps are repeated and the model parameters are updated until convergence.

Various embodiments are directed to a different number of bands in the k.p model.

In the following, the bulk silicon six-band k.p model parameter extraction is used as an example, to show how the simplex optimization algorithm works in the extraction.

In this example, the calculation is done in the Nd-dimensional (Nd=4) parameter space, since there are four parameters to optimize. To start with, (0, 0, 0, 0) is used as the initial guess of the model parameters (γ1, γ2, γ3 and Δso). A simplex with Nd+1 vertices $Xi(x_{i1}^{(0)}, x_{i2}^{(0)}, x_{i3}^{(0)}, x_{i4}^{(0)})$ is formed surrounding the initial guess, where the superscript means the iteration step number and i=1, 2, . . . , Nd+1 is the vertex label. Then, the second and third steps are executed to obtain the cost function values (ci) for all vertices. After sorting, the vertex (Xm) with the largest cost function value (cm) will be updated.

To update Xm, Xm is reflected with respect to the geometric average of all other vertices, to obtain the reflected image Xr. Then, the cost function value (cr) of Xr is evaluated using the second and third steps. According to the value of cr, the vertex is updated differently in the following three different situations.

If $\min_{i \neq m}\{c_i\} \leq c_r \leq \max_{i \neq m}\{c_i\}$,

Then the vertex Xm is updated as Xr.

If $c_r \leq \min_{i \neq m}\{c_i\}$,

Then it means that the trial Xr is on the correct update direction in the parameter space to reduce cost function but the reflection length may be too short to be optimal. Then the reflection is extended by twice as X'r whose cost function value is c'r. If c'r is smaller than cr, the vertex Xm is updated as X'r. If c'r is larger than cr, the vertex Xm is updated as Xr. If $c_r > \max_{i \neq m}\{c_i\}$ it means that the trial Xr is on the wrong update direction in the parameter space. Then the search direction is reversed as Xm−Xr, The reversed search is repeated until $c_r < \max_{i \neq m}\{c_i\}$ is satisfied.

The above calculations continues iteratively until either the difference between the maximum cost function values of the two adjacent iteration steps is smaller than a floor, e.g. 1 meV, or the maximum distance between any two vertices in the simplex is smaller than a floor, e.g. 1e-6.

Results can converge in a stepwise way to the experimentally measured values, with a mismatch one the other of, for example, several percent in the final converged results, due to the fact that DFT results are approximations of physical reality.

Figure 3:
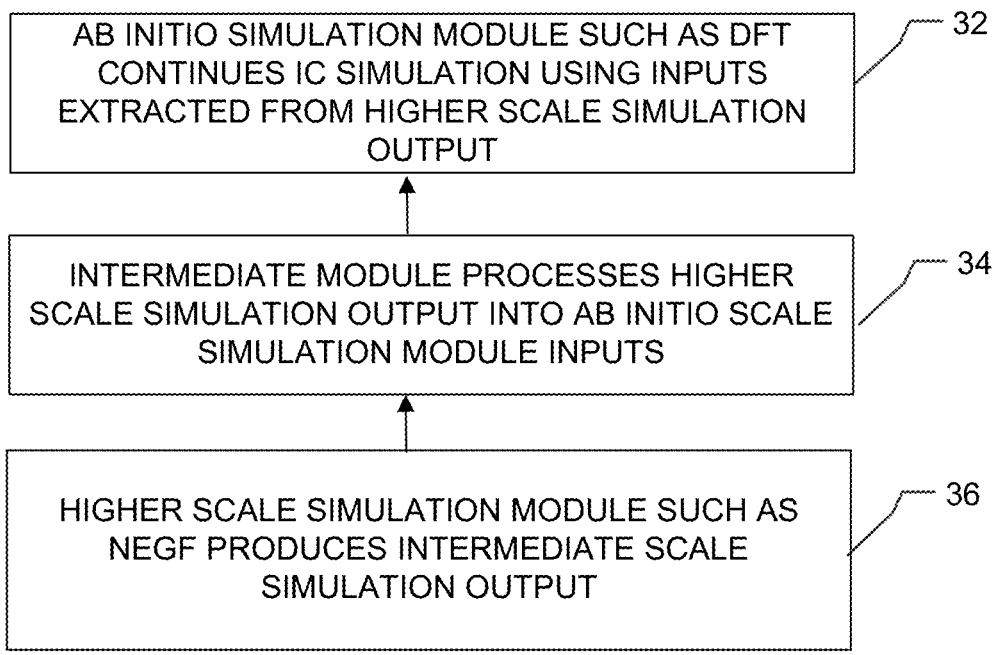
FIG. 3 is an example block diagram of simulation modules at multiple simulation scales coupled together via an intermediate module using output of a higher scale simulation module as input for an ab initio simulation module.

FIG. 3 is an example block diagram of simulation tools at multiple simulation scales coupled together via an extraction tool using output of a higher scale simulation tool as input for an ab initio simulation tool. To take advantage of the accuracy of more granular simulation, and the lowered computation intensity of less granular simulation, parameters are passed between multiple levels of simulation. Such embodiments provide data from simpler/large scale tools to the more sophisticated/small scale tools to accurately evaluate effects on the microscopic scale.

Although the example discusses NEGF as the larger scale simulation tool, other embodiments are directed to other larger scale simulation tools other than NEGF. Although NEGF and DFT are discussed, other modules can be substituted.

At 36, results are produced from an intermediate scale IC simulation tool such as NEGF. At 34, results are processed into lower simulation scale input. Processing can be as minimal as passing a parameter, or performing multiple operations to extract data. At 32, the simulation is continued using the results from the intermediate scale tool as input of an ab initio simulation tool such as DFT.

The non-equilibrium Green's function (NEGF) is an important algorithm in the TCAD tools and methodologies we propose here. The NEGF module can be used to simulate the transport properties of the devices, e.g. current, potential distribution, transmission coefficient, etc. Therefore, it is a vital part of the proposed TCAD tools.

The NEGF simulator is based on iterative self-consistent solution of the Green's functions, the self-energies, and the potential profile. In the NEGF simulator, the calculation starts from the Hamiltonian matrix H, which can be obtained from either ab initio density functional theory (DFT) simulations, or tight binding parameterization, or effective mass approximation, or other techniques.

The steps are explained in more details below:

1. The contact self-energies are used to represent the electrodes/contacts (like source and drain) that are linked to the transport channel. It is evaluated iteratively at energy points of interests, by using exponentially converging contact self-energy Green's function algorithms.

2. To start with, the potential profile is used as an initial guess of the final converged potential profile. The typical choice is a linear drop from drain to source. Of course, other initial guess shapes are allowed. The principle of choosing the initial potential profile is that it should be as close to the final converged potential profile as possible, in order to reduce the iteration number and computational cost to achieve convergence.

3. The retarded Green's function $G^r$, the election Green's function $G^n$, and the hole Green's function $G^p$ are evaluated at all energy points of interests, by using numerical algorithms like (but not limited to) matrix factorization, recursive Green's function algorithm, and the Fast inverse using nested dissection, etc. The proposed approach uses efficient algorithms to accelerate the calculation by taking advantage of the special matrix structure of the Hamiltonian.

4. The in-scattering and out-scattering self-energies are computed by using the Green's functions, which are computed in the previous step. These scattering self-energies are used to represent the various scattering mechanism during transport.

5. The convergence check is performed to determine whether or not the calculation of the scattering has converged. If no, more self-consistent calculation loops will be performed. If yes, the calculation continues to the next step.

6. Poisson's equation is calculated using the algorithms like, but not limited to, direct matrix computation algorithms, iterative Krylov subspace matrix computation algorithms, fast Fourier transform, and fast multipole method, domain decomposition method, etc. The purpose is to obtain the updated potential profile from the known charge distribution.

7. The convergence check is performed to determine whether or not the potential profile calculation has converged. If no, more iteration loops will be performed. If yes, the calculation continues to the post-process module.

8. The post-process module calculates the physical quantities of interest, which includes (but not limited to), current density, current-voltage curve, transmission coefficient, density of states, potential profile, charge distribution, etc.

Figure 4:
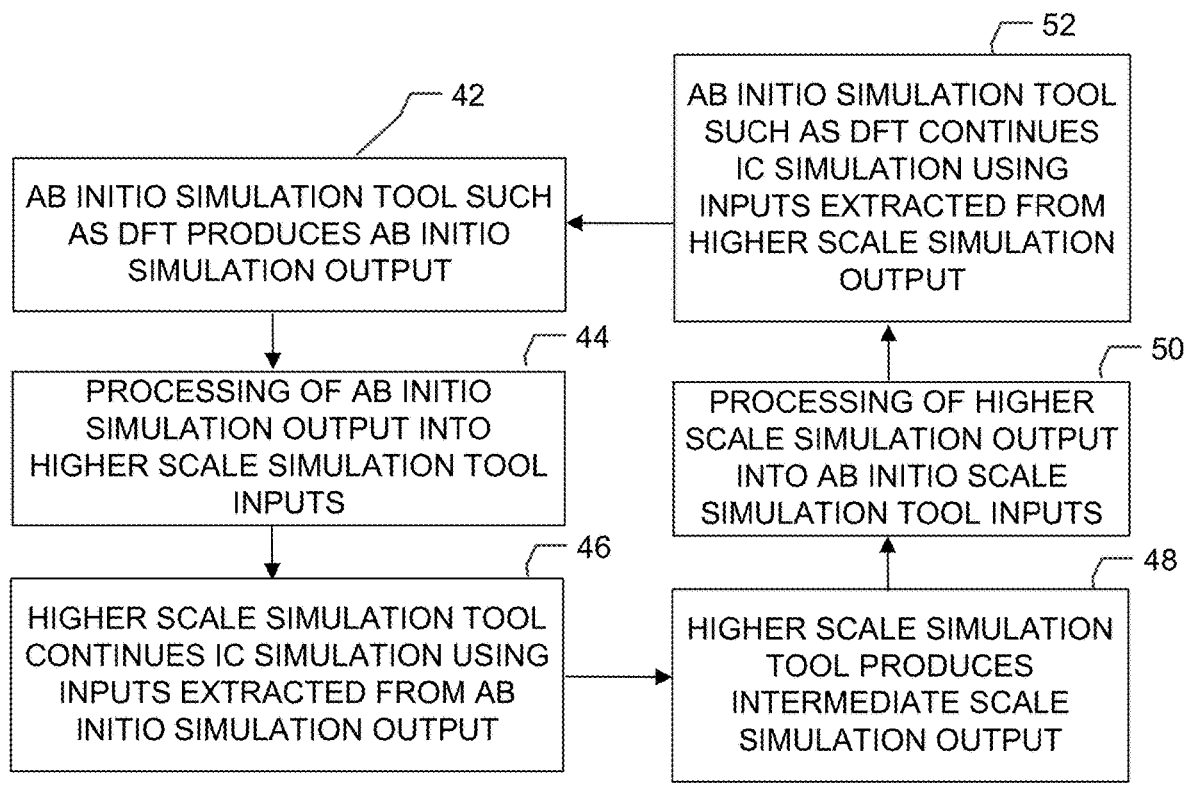
FIG. 4 is an example block diagram of simulation modules at multiple simulation scales coupled together via intermediate module processing, to iterate between an ab initio simulation module and a higher scale simulation module.

FIG. 4 is an example block diagram of simulation tools at multiple simulation scales coupled together via intermediate tools to iterate between an ab initio simulation tool and a higher scale simulation tool. The block diagram of 42, 44, 46, 48, 50 and 52 essentially combines FIGS. 2 and 3. In addition to one-way hierarchical modeling flow from more sophisticated/small scale tools down to the simpler/large scale tools, one or several iterations can be performed by going in both directions along that hierarchy. Such feedback and iterations can be applied across two or more levels of the model, potentially spanning the range from circuit/system level to the first principles level. To take advantage of the accuracy of more granular simulation, and the lowered computation intensity of less granular simulation, parameters are passed between multiple levels of simulation.

An iterative and self-adaptive scheme (mentioned as the "scheme" hereafter) of the parameterization process of the phenomenological simulation modules and methodologies, is used to simulate the fabrication and operation of integrated circuit devices. The scheme combines the strengths of the ab initio simulation modules and methodologies, which are comparatively more accurate but computationally expensive, and the merits of the phenomenological simulation modules and methodologies, which are relatively less accurate but computationally inexpensive, to offer a set of iterative, self-adaptive, and automated simulation and design tools and methodologies.

The "iterative parameterization" mentioned above covers multiple different categories of iterative processes. Iterative process (i) refers to the iterative parameter extraction between/among the modules mentioned in the above two points. Iterative process (ii) refers to the iterative parameter extraction between the "top-down approach", which means that the physical quantities to be calculated are expressed as phenomenological equations with the phenomenological parameters extracted from the ab initio simulations, and the "bottom-up approach", which means that the calculation starting point is the ab initio equations and the computational expenses are alleviated by approximating some computationally expensive components in the equations.

Although NEGF and DFT are discussed, other modules can be substituted.

In an iterative looped feedback, the NEGF module and the DFT module are combined together to provide enhanced simulation capabilities, in two directions. The NEGF module outputs non-equilibrium transport properties and electronic structure information, which are used in the DFT module to account for the non-equilibrium conditions. The DFT module outputs equilibrium electronic structure information, which is used in the NEGF module to simulate transport properties. These two directions iterate as a bi-directional feedback loop, to offer unprecedented TCAD simulation capabilities. For example, to simulate the source-channel-drain device structure, the DFT module is first run to obtain the Hamiltonian and overlap matrices. Then these matrices are input into the NEGF module to simulate the transport properties. This generates the non-equilibrium electron transport properties like potential distribution, which in turn is fed back into the DFT module to calculate physical properties like forces on atoms and the internal stress under non-equilibrium conditions, etc.

Different types of an iterative process are as follows: (1) simulation functionality feedback; (2) calculation efficiency and precision feedback; and (3) the iterative looped feedback. Although NEGF and DFT are discussed, other modules can be substituted. They are introduced in the three following sections below:

In the simulation functionality feedback, The NEGF module decides what should be calculated and sends instructions to the lower-level DFT module to get the computations done. For example, in the ab initio electron transport simulation, the NEGF module uses ab initio Hamiltonian matrix and overlap matrix as input. So the NEGF module sends instructions to the DFT module, requesting related calculations. In the effective mass Hamiltonian electron transport calculations, the NEGF module can request the DFT module to perform band structure calculations and extract the effective mass.

In the efficiency and precision feedback, the NEGF module runs electron transport simulations and compares the results against benchmark results. The comparison is used to feedback into the DFT module, to strike a good balance between the computational efficiency and precision. For instance, the calculation is largely determined by the size of the matrix that represents the system of interests. The larger the matrix size, the more precise the results are. But the calculation will be less efficient. In contrast, if the system is represented by using smaller matrices, the calculation will be less precise, but the calculation will be more efficient. By comparing against benchmark results and/or experimental calibrations of example systems, the NEGF module can work jointly with the lower-level DFT module, to determine the optimum matrix size to represent the target system. By using this optimum matrix size, the simulation can achieve both good calculation precision and high simulation efficiency.

The three processes introduced above are designed to be automated and self-adaptive, in order to minimize the human intervention and to maximize productivity.

Figure 5:
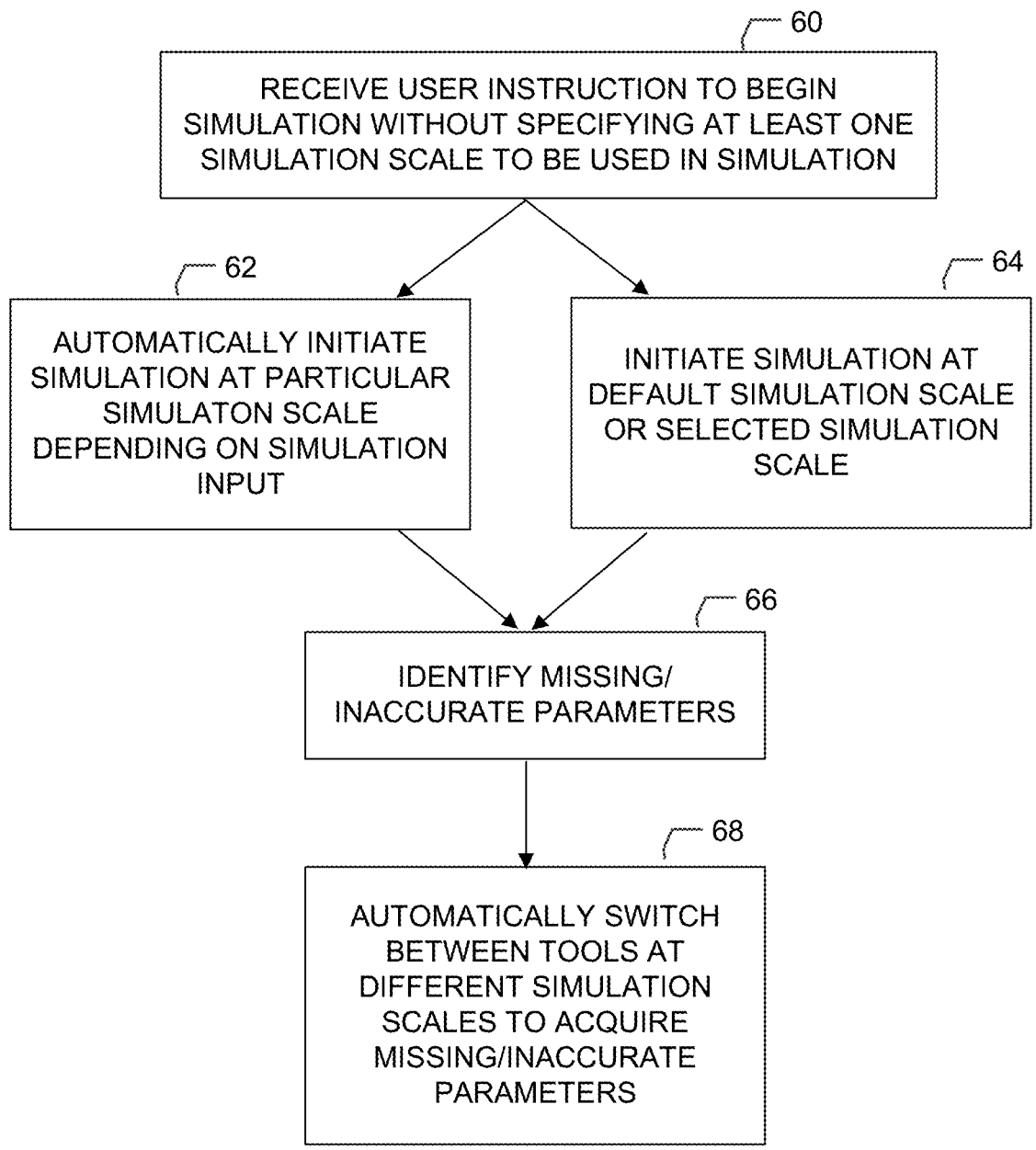
FIG. 5 is an example process flow of executing simulation tools automatically at multiple simulation scales, to improve inaccurate input (such as missing input).

FIG. 5 is an example process flow of executing simulation tools automatically at multiple simulation scales, to improve inaccurate input (such as missing input).

Multiple simulation scales of various simulation modules, such as in FIG. 1, use output of one module as input for another module, and automatically executing another module at the same simulation scale or different simulation scale to improve inaccurate input (such as missing input).

In the example of FIG. 1, if a particular simulation module has missing input, the coordination module executes another module to provide the missing input. If a particular simulation scale is not specified in the execution instruction, the coordination module determines the appropriate scales to run. The proposed modules receive target simulation quantities via a user interface, and instruct the coordination module to start the simulation.

At 60, a user (or automated) instruction is received to begin simulation without specifying at last one simulation scale (or at least without specifying one simulation tool). There are multiple options. In option 62, simulation is initiated automatically at a particular simulation scale (or a particular simulation tool out of many) depending on simulation input that does not specify the particular simulation scale (or depending on simulation input that does not specify does not specify the particular simulation tool). In option 64, simulation is initiated at a default simulation scale without regard to other simulation input (or initiated with a default simulation module without regard to other simulation input), or with regard to an explicitly selected simulation scale (or with regard to an explicitly selected simulation module). At 66, inaccurate parameters (such as missing parameters) are identified. At 68, simulation scales (or simulation tools) are automatically switched to acquire inaccurate parameters such as missing parameters.

Figure 6:
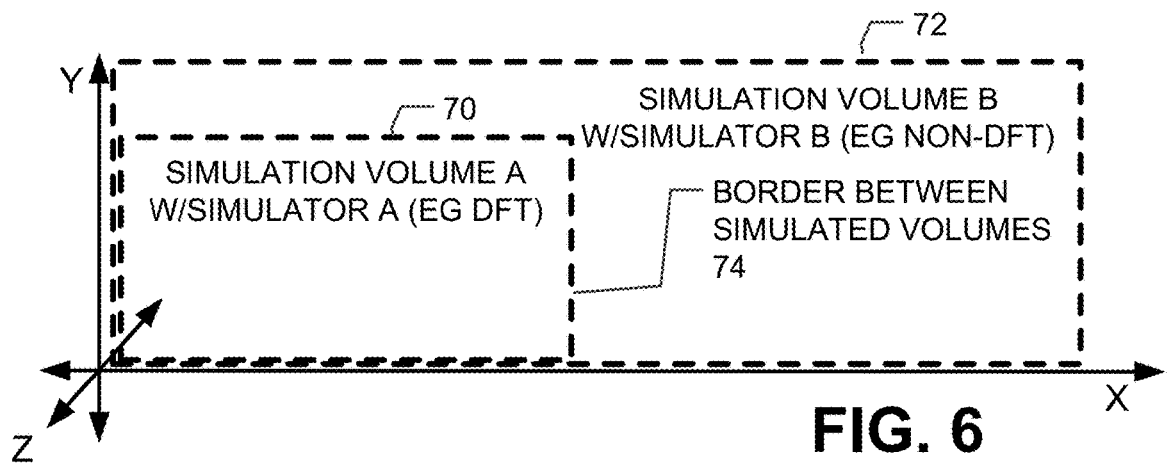
FIG. 6 shows different simulation volumes of simulation modules at different simulation scales.

FIG. 6 shows different simulation volumes of simulation modules at different simulation scales. A 3D simulation volume is indicated. In other embodiments, the simulation volume may be 2D or 1D. Because simulator A has more granularity than simulator B, simulation volume A 70 of simulator A is smaller than simulation volume B 72 of simulator B. Because simulation volume A 70 is smaller, the border between simulation volumes A and B is also a border 70 of simulation volume A 70.

Figure 7:
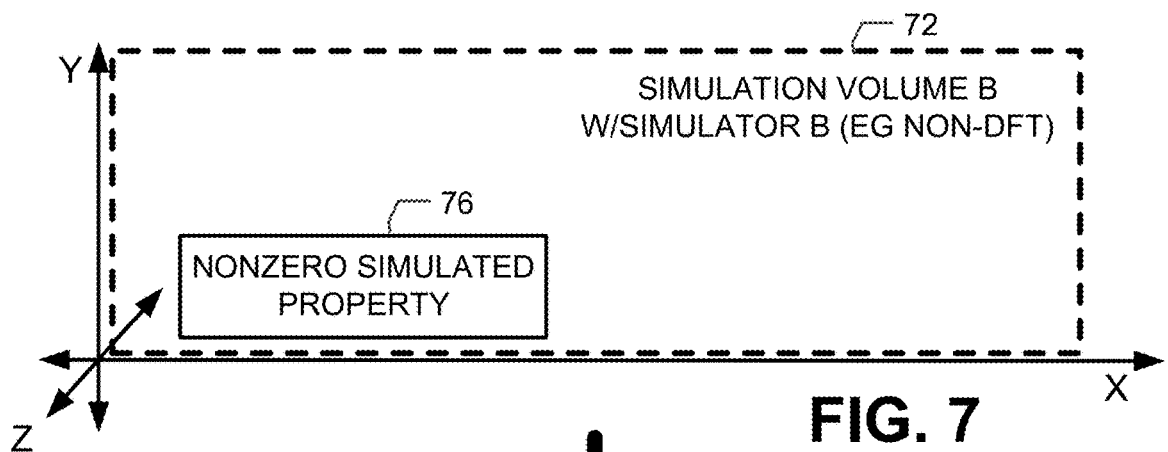
FIGS. 7-8 shows a switch between simulation modules at different simulation scales, from a larger simulation volume to a smaller simulation volume.
Figure 8:
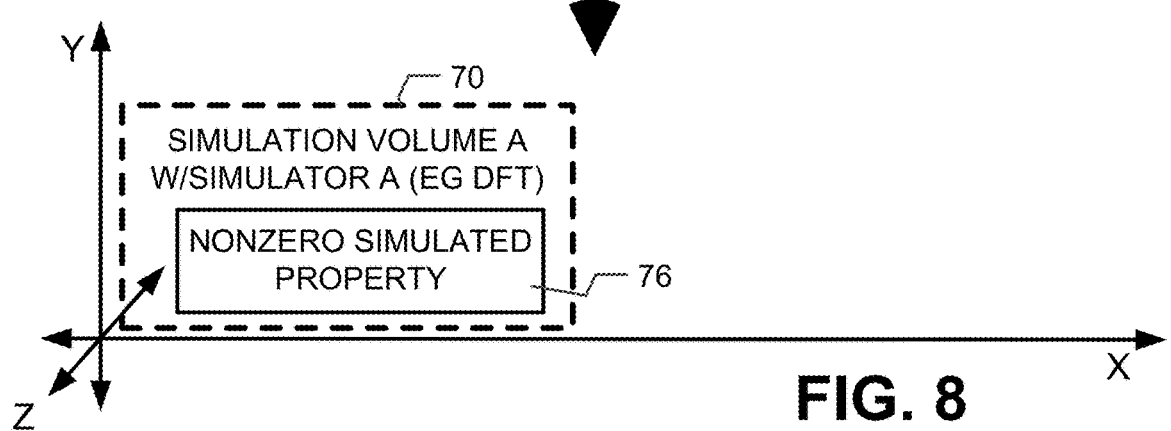

FIGS. 7-8 shows a switch between simulation modules at different simulation scales, from a larger simulation volume to a smaller simulation volume. In FIG. 7, nonzero simulated property 76 occupies a relatively small fraction of simulation volume B 72. In FIG. 8, nonzero simulated property 76 occupies a relatively large fraction of simulation volume A 70. Accordingly, the simulation modules/scales switch automatically from simulation volume B 72 of simulator B to simulation volume A 70 of simulator A.

Figure 9:
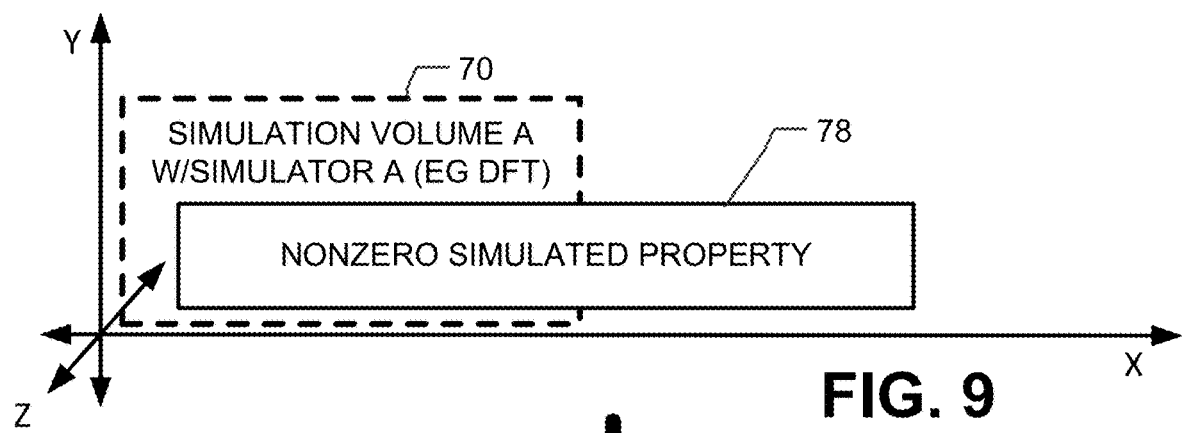
FIGS. 9-10 shows a switch between simulation module volumes, with horizontal and oblique asymptotes.
Figure 10:
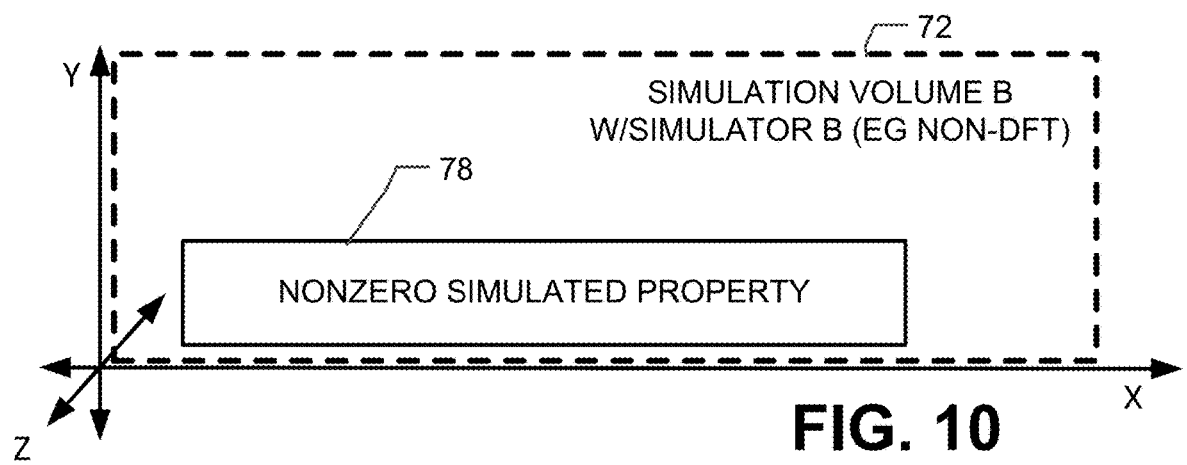

FIGS. 9-10 shows a switch between simulation module volumes from a smaller simulation volume to a larger simulation volume. In FIG. 9, nonzero simulated property 76 is not fully captured by simulation volume A 70. In FIG. 10, nonzero simulated property 76 occupies fits in simulation volume B 72. Accordingly, the simulation modules/scales switch automatically from simulation volume A 70 of simulator A to simulation volume B 72 of simulator B.

Examples of a simulated property include: electrostatic potential, electric field, non-equilibrium charge distribution, stress distribution and stress gradient, strain distribution and strain gradient, electron and hole generation, electron and hole recombination, atomic migration (such as hydrogen, lattice atoms, and impurities), point defect formation, extended defect formation, void formation, ionic migration, filament formation, phase change (such as between crystal and amorphous states), non-equilibrium spin distribution, electron and hole trapping at the defects, Joule heat generation, structure changes due to atomic and molecular chemical reactions, and optically generated electrons and holes. Such properties can be converted to DFT inputs.

Figure 11:
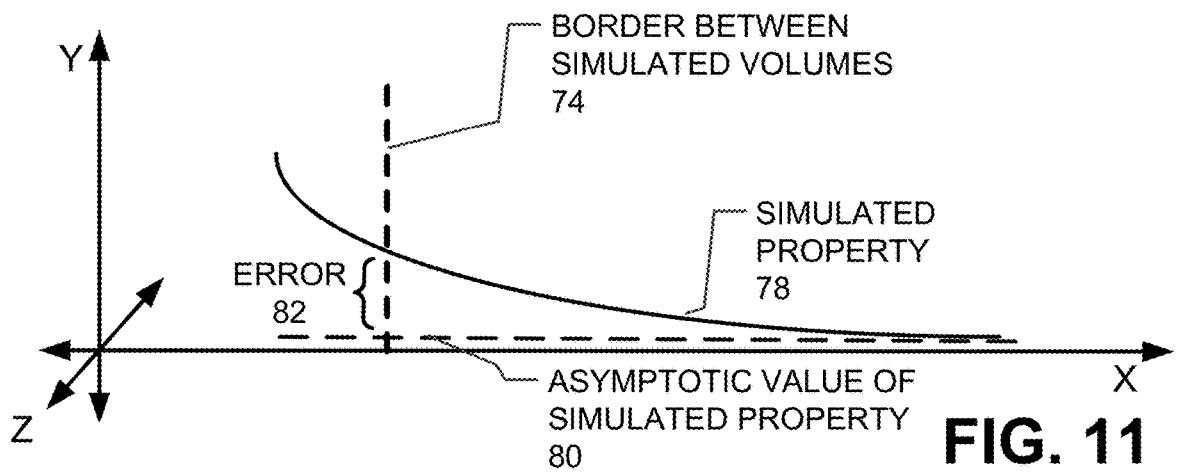
FIGS. 11-12 show an error at the border between simulation modules at different simulation scales, from a smaller simulation volume to a larger simulation volume.
Figure 12:
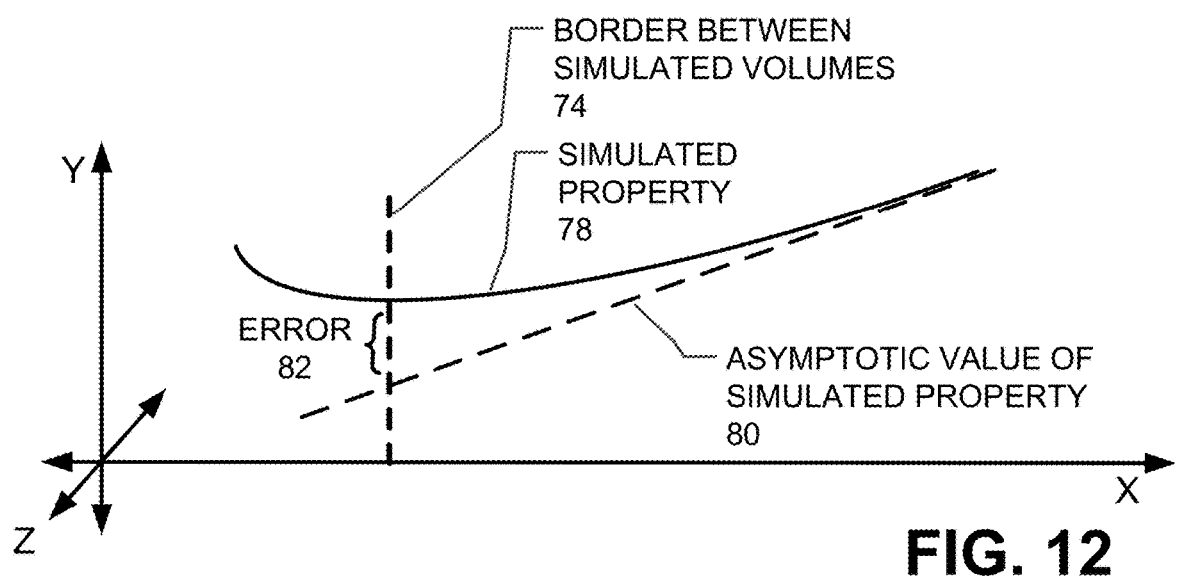

FIGS. 11-12 show an error at the border between simulation modules at different simulation scales, with horizontal and oblique asymptotes.

In the example of FIGS. 9-10, a nonzero simulated property was not fully captured by simulation volume A of simulator A, so the simulation modules/scales switch automatically to simulation volume B 72 of simulator B. However, an alternative is to not switch and tolerate the nonzero error, remaining with simulation volume A of simulator A so long as the nonzero error does not exceed an error threshold.

FIG. 11 shows that at the border 74 between simulation volumes A and B, an error 82 exist in the nonzero simulated property 78. The nonzero simulated property 78 has failed to reach the horizontally asymptotic value 80 of the nonzero simulated property 78. In FIG. 12, the nonzero simulated property 78 has failed to reach the obliquely asymptotic value 80 of the nonzero simulated property 78. So long as the error 82 does not does not exceed an error threshold, the nonzero error may be tolerated by not switching from simulation volume A of simulator A to simulation volume B 72 of simulator B.

FIGS. 13A, 13B, 13C and 13D illustrate various lattice configurations, as examples of arrangements in which a semiconductor property has a finite distortion range to be simulated as in FIGS. 6-12. The finite distortion range can depend on the direction. Distortions can be electrical, mechanical, or band structure. Examples include point defects such as vacancy defects, interstitial defects and substitutional defects, using a GaAs alloy as an example. A conventional 8-atom cell (e.g. 400), and a supercell composed of 4 conventional cells are shown in each of the figures. As used herein, a host is the material into which native defects and dopants diffuse, and a host atom is an atom in the host material without any diffusion into the host material. The host material can be an alloy.

Figure 13A:
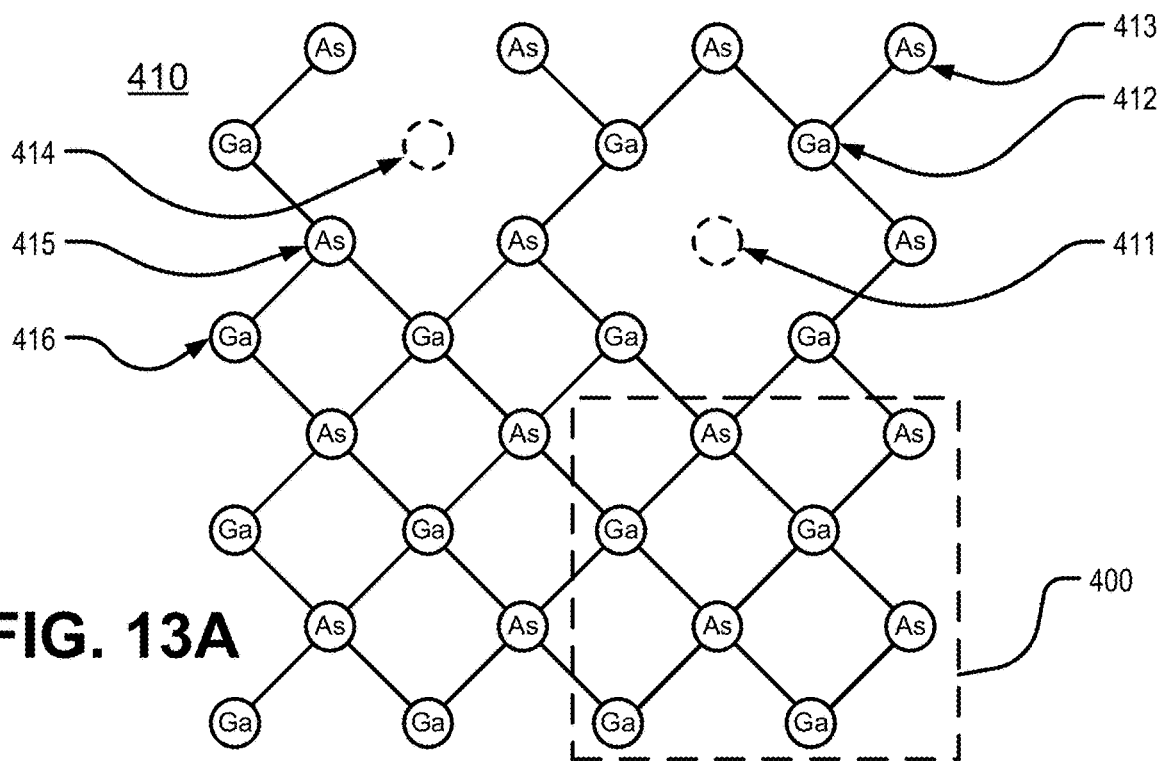
FIGS. 13A, 13B, 13C and 13D illustrate various lattice configurations, as examples of arrangements in which a semiconductor property has a finite distortion range.

FIG. 13A illustrates a supercell 410 including host atoms Ga (Gallium) and As (Arsenic), and lattice vacancy defects (e.g. 411, 414) surrounded by adjacent host atoms Ga and As. A lattice vacancy defect refers to an atom site in a crystal lattice where a single host atom is missing. Neighbors of a point defect can be important. As shown in the example of FIG. 13A, a vacancy defect has first order neighbors and second order neighbors. For instance, vacancy defect 411 at an As site has 4 first-order neighbors that are Ga atoms (e.g. 412), and more second-order neighbors (e.g. 413). Vacancy defect 414 at a Ga site has 4 first-order neighbors that are As atoms (e.g. 415), and more second-order neighbors (e.g. 416).

In a different alloy there can be more options for first-order neighbors. For instance in a SiGe alloy (not shown), a point defect such as a vacancy defect can have different first-order neighbors including 4 Si atoms, 3 Si atoms and 1 Ge atom, 2 Si atoms and 2 Ge atoms, 1 Si and 3 Ge atoms, or 4 Ge atoms.

Figure 13B:
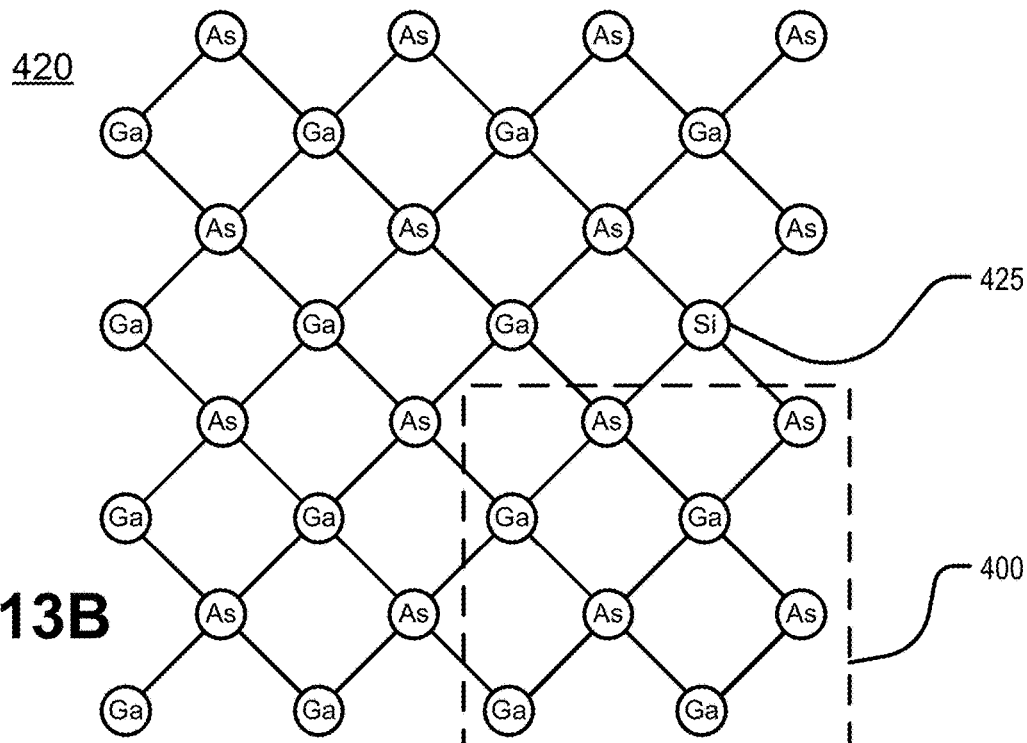

FIG. 13B illustrates an example of a dopant atom surrounded by various different numbers of host atoms adjacent thereto. Impurities or dopants can be doped into the GaAs host material. Group IV elements such as Si (silicon) can act as either donors on Ga sites or acceptors on As sites. In the example of FIG. 13B, Si is used as the dopant (e.g. 425).

Figure 13C:
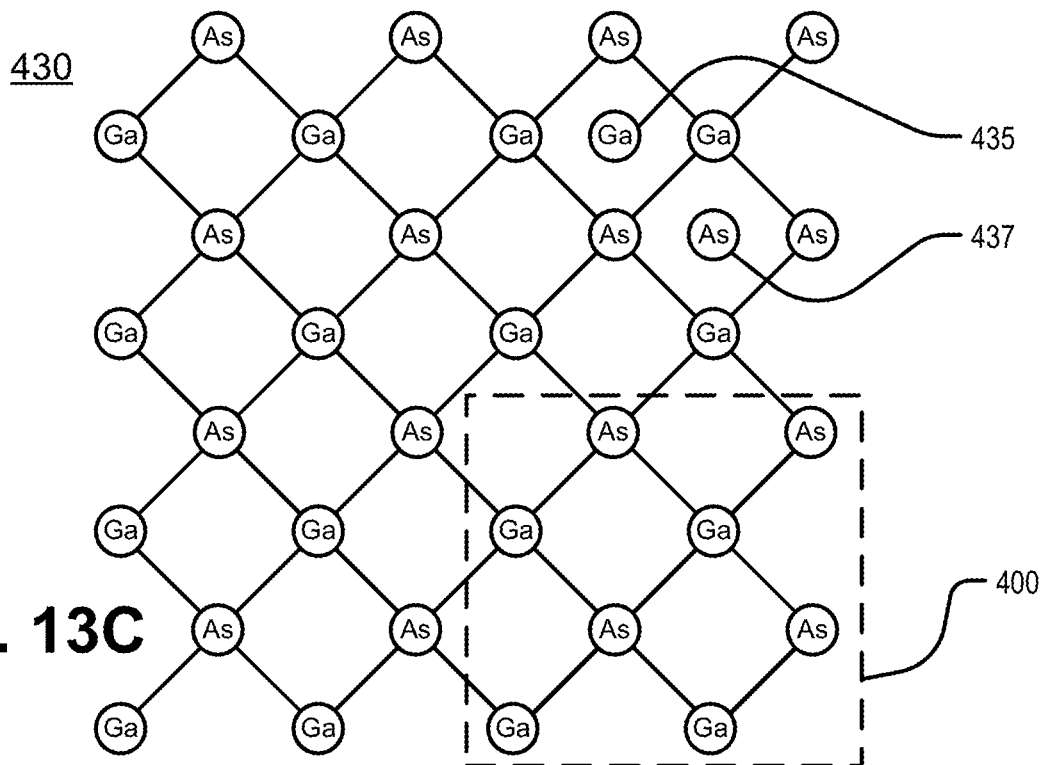

FIG. 13C illustrates an example of an interstitial defect atom surrounded by various different numbers of host atoms adjacent thereto, where an interstitial defect atom is present in the interstitial spaces between the host crystal lattice sites. In an alloy (e.g. GaAs), each alloying species (e.g. Ga, As) can be at a defect site between lattice sites or an interstitial location off the crystal lattice. In the example of FIG. 13C, a Ga interstitial is at a defect site (e.g. 435), while an As interstitial is at another defect site (e.g. 437). In a tetrahedrally coordinated GaAs configuration (not shown), a Ga interstitial or a As interstitial can have four equidistant first-order neighbors. In a hexagonally coordinated GaAs configuration (not shown), a Ga interstitial or a As interstitial can have six equidistant first-order neighbors, including 3 Ga atoms and 3 As atoms.

Figure 13D:
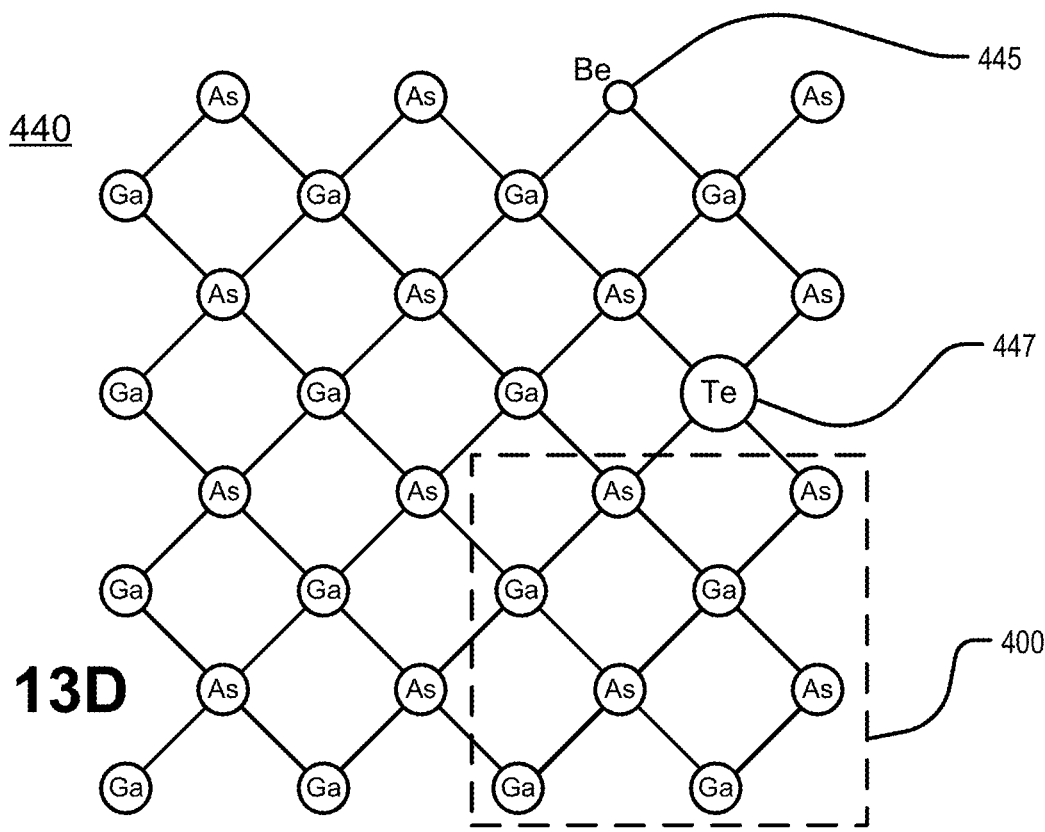

FIG. 13D illustrates an example of a substitutional defect atom surrounded by various different numbers of host atoms adjacent thereto, where a host atom is replaced by an atom of a different type than the host atoms. A substitutional defect atom can be smaller or larger than a host atom (covalent radius of Ga=126 pm, covalent radius of As=119 pm). In the example of FIG. 13D, Be (Beryllium, covalent radius=90 pm) is shown as a smaller substitutional defect atom at a defect site (e.g. 445), while Te (Tellurium, covalent radius=135 pm) is shown as a larger substitutional defect atom at another defect site (e.g. 447).

For a more complex material, there can be more types of point defects. For instance, indium gallium arsenide (In-GaAs) is a ternary alloy of indium, gallium and arsenic. Indium and gallium are both from the boron group (group III) of elements, and thus have similar roles in chemical bonding. InGaAs is regarded as an alloy of gallium arsenide and indium arsenide with properties intermediate between the two depending on the proportion of gallium to indium. For instance, compounds In0.75Ga0.25As, In0.5Ga0.5As, and In0.25Ga0.75 include different proportions of gallium to indium, while InAs does not include Ga and GaAs does include In.

In InGaAs, point defects can include As vacancy (i.e. missing lattice atom where As is supposed to be), In/Ga vacancy (i.e. missing lattice atom where In or Ga is supposed to be), As interstitial (i.e. extra As atom between lattice sites), In interstitial (i.e. extra In atom between lattice sites), Ga interstitial (i.e. extra Ga atom between lattice sites), As atom in the In/Ga lattice site, In atom in the As lattice site, and Ga atom in the As lattice site. For each of these point defects, there are different combinations of first-order neighbors, similar to the first-order neighbors described for the SiGe alloy.

Figure 14:
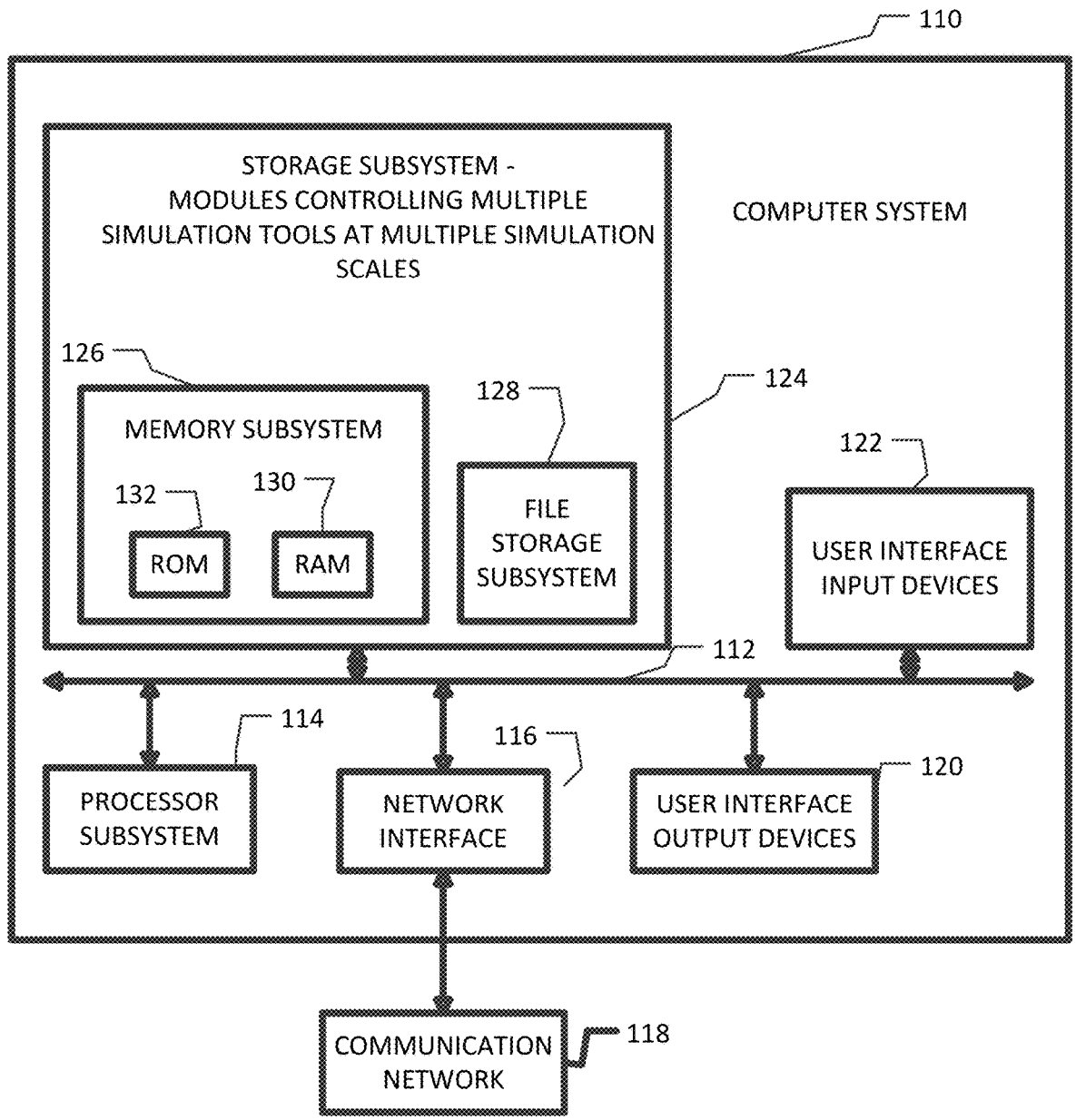
FIG. 14 is a simplified block diagram of a computer system configured to perform IC simulation at multiple scales.

FIG. 14 is a simplified block diagram of a computer system configured to perform IC simulation to implement any of the methods and processes herein.

Computer system 110 typically includes a processor subsystem 114 which communicates with a number of peripheral devices via bus subsystem 112. These peripheral devices may include a storage subsystem 124, comprising a memory subsystem 126 and a file storage subsystem 128, user interface input devices 122, user interface output devices 120, and a network interface subsystem 116. The storage subsystem 128 includes non-transitory memory storing computer programs, databases and other resources to configure the data processing systems as tool for controlling multiple simulation tools at multiple simulation scales as described herein. The tool can include an API configured to use input parameter sets, and to perform the procedures of the tool using the input parameter sets.

The input and output devices allow user interaction with computer system 110. Network interface subsystem 116 provides an interface to outside networks, including an interface to communication network 118, and is coupled via communication network 118 to corresponding interface devices in other computer systems. Communication network 118 may comprise many interconnected computer systems and communication links. These communication links may be wireline links, optical links, wireless links, or any other mechanisms for communication of information, but typically it is an IP-based communication network. While in one embodiment, communication network 118 is the Internet, in other embodiments, communication network 118 may be any suitable computer network.

The physical hardware component of network interfaces are sometimes referred to as network interface cards (NICs), although they need not be in the form of cards: for instance they could be in the form of integrated circuits (ICs) and connectors fitted directly onto a motherboard, or in the form of macrocells fabricated on a single integrated circuit chip with other components of the computer system.

User interface input devices 122 may include a keyboard, pointing devices such as a mouse, trackball, touchpad, or graphics tablet, a scanner, a touch screen incorporated into the display, audio input devices such as voice recognition systems, microphones, and other types of input devices. In general, use of the term "input device" is intended to include all possible types of devices and ways to input information into computer system 110 or onto computer network 118.

User interface output devices 120 may include a display subsystem, a printer, a fax machine, or non visual displays such as audio output devices. The display subsystem may include a cathode ray tube (CRT), a flat panel device such as a liquid crystal display (LCD), a projection device, or some other mechanism for creating a visible image. The display subsystem may also provide non visual display such as via audio output devices. In general, use of the term "output device" is intended to include all possible types of devices and ways to output information from computer system 110 to the user or to another machine or computer system.

Storage subsystem 124 stores the basic programming and data constructs that provide the functionality of certain embodiments of the present invention. For example, the various modules implementing the functionality of certain embodiments of the invention may be stored in storage subsystem 124. These software modules are generally executed by processor subsystem 114.

Memory subsystem 126 typically includes a number of memories including a main random access memory (RAM) 130 for storage of instructions and data during program execution and a read only memory (ROM) 132 in which fixed instructions are stored. File storage subsystem 128 provides persistent storage for program and data files, and may include a hard disk drive, a floppy disk drive along with associated removable media, a CD ROM drive, an optical drive, or removable media cartridges. The databases and modules implementing the functionality of certain embodiments of the invention may have been provided on a computer readable medium such as one or more CD-ROMs, and may be stored by file storage subsystem 128. The host memory 126 contains, among other things, computer instructions which, when executed by the processor subsystem 114, cause the computer system to operate or perform functions as described herein. As used herein, processes and software that are said to run in or on "the host" or "the computer", execute on the processor subsystem 114 in response to computer instructions and data in the host memory subsystem 126 including any other local or remote storage for such instructions and data.

Bus subsystem 112 provides a mechanism for letting the various components and subsystems of computer system 110 communicate with each other as intended. Although bus subsystem 112 is shown schematically as a single bus, alternative embodiments of the bus subsystem may use multiple busses.

Computer system 110 itself can be of varying types including a personal computer, a portable computer, a workstation, a computer terminal, a network computer, a television, a mainframe, a server farm, or any other data processing system or user device. Due to the ever changing nature of computers and networks, the description of computer system 110 is intended only as a specific example for purposes of illustrating the preferred embodiments of the present invention. Many other configurations of computer system 110 are possible having more or less components than the computer system.

In addition, while the present invention has been described in the context of a fully functioning data processing system, those of ordinary skill in the art will appreciate that the processes herein are capable of being distributed in the form of a computer readable medium of instructions and data and that the invention applies equally regardless of the particular type of signal bearing media actually used to carry out the distribution. As used herein, a computer readable medium is one on which information can be stored and read by a computer system. Examples include a floppy disk, a hard disk drive, a RAM, a CD, a DVD, flash memory, a USB drive, and so on. The computer readable medium may store information in coded formats that are decoded for actual use in a particular data processing system. A single computer readable medium, as the term is used herein, may also include more than one physical item, such as a plurality of CD ROMs or a plurality of segments of RAM, or a combination of several different kinds of media. As used herein, the term does not include mere time varying signals in which the information is encoded in the way the signal varies over time.

Figure 15:
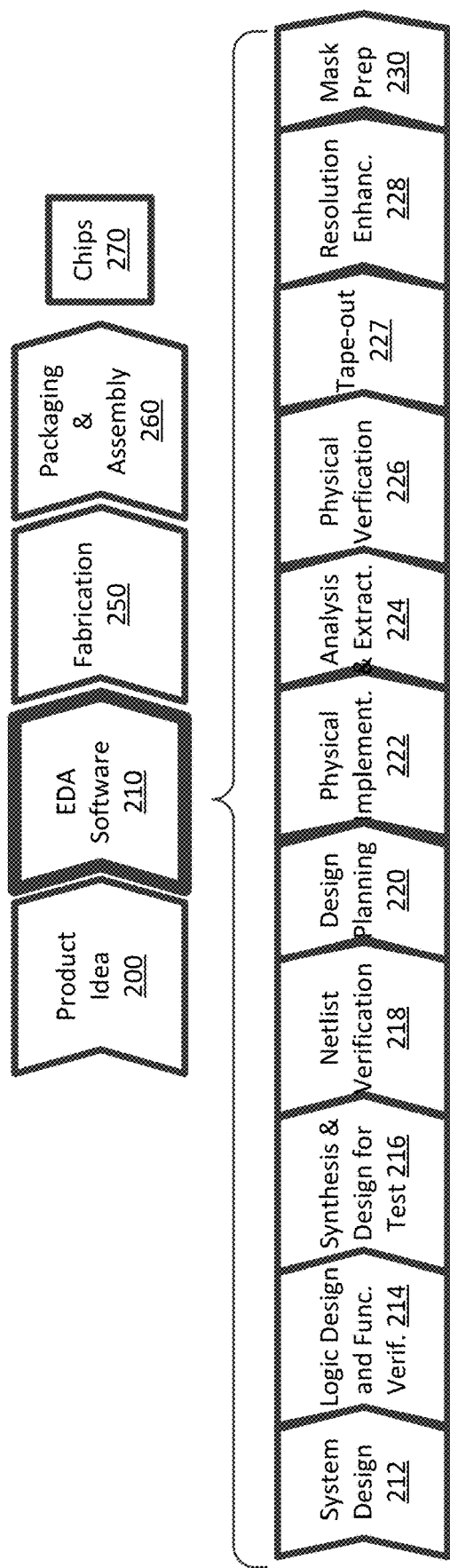
FIG. 15 illustrates EDA tools and process flow for integrated circuit design and manufacturing.

FIG. 15 illustrates EDA tools and process flow for integrated circuit design and manufacturing.

Aspects of the invention can be used to support an integrated circuit design flow. At a high level, the process starts with the product idea (step 200) and is realized in an EDA (Electronic Design Automation) software design process (step 210). When the design is finalized, it can be taped-out (step 227). At some point after tape out, the fabrication process (step 250) and packaging and assembly processes (step 260) occur resulting, ultimately, in finished integrated circuit chips (result 270).

The EDA software design process (step 210) is itself composed of a number of steps 212-230, shown in linear fashion for simplicity. In an actual integrated circuit design process, the particular design might have to go back through steps until certain tests are passed. Similarly, in any actual design process, these steps may occur in different orders and combinations. This description is therefore provided by way of context and general explanation rather than as a specific, or recommended, design flow for a particular integrated circuit.

A brief description of the component steps of the EDA software design process (step 210) will now be provided.

System design (step 212): The designers describe the functionality that they want to implement, they can perform what-if planning to refine functionality, check costs, etc. Hardware-software architecture partitioning can occur at this stage. Example EDA software products from Synopsys, Inc. that can be used at this step include Model Architect, Saber, System Studio, and DesignWare® products.

Logic design and functional verification (step 214): At this stage, the VHDL or Verilog code for modules in the system is written and the design is checked for functional accuracy. More specifically, the design is checked to ensure that it produces correct outputs in response to particular input stimuli. Example EDA software products from Synopsys, Inc. that can be used at this step include VCS, VERA, DesignWare®, Magellan, Formality, ESP and LEDA products.

Synthesis and design for test (step 216): Here, the VHDL/Verilog is translated to a netlist. The netlist can be optimized for the target technology. Additionally, the design and implementation of tests to permit checking of the finished chip occurs. Example EDA software products from Synopsys, Inc. that can be used at this step include Design Compiler®, Physical Compiler, DFT Compiler, Power Compiler, FPGA Compiler, TetraMA1, and DesignWare® products.

Netlist verification (step 218): At this step, the netlist is checked for compliance with timing constraints and for correspondence with the VHDL/Verilog source code. Example EDA software products from Synopsys, Inc. that can be used at this step include Formality, PrimeTime, and VCS products.

Design planning (step 220): Here, an overall floor plan for the chip is constructed and analyzed for timing and top-level routing. Example EDA software products from Synopsys, Inc. that can be used at this step include Astro and Custom Designer products.

Physical implementation (step 222): The placement (positioning of circuit elements) and routing (connection of the same) occurs at this step, as can selection of library cells to perform specified logic functions. Example EDA software products from Synopsys, Inc. that can be used at this step include the Astro, IC Compiler, and Custom Designer products.

Analysis and extraction (step 224): At this step, the circuit function is verified at a transistor level, this in turn permits what-if refinement. Example EDA software products from Synopsys, Inc. that can be used at this step include Astro-Rail, PrimeRail, PrimeTime, and Star-RC1T products.

Physical verification (step 226): At this step various checking functions are performed to ensure correctness for:

manufacturing, electrical issues, lithographic issues, and circuitry. Example EDA software products from Synopsys, Inc. that can be used at this step include the Hercules product.

Tape-out (step 227): This step provides the "tape out" data to be used (after lithographic enhancements are applied if appropriate) for production of masks for lithographic use to produce finished chips. Example EDA software products from Synopsys, Inc. that can be used at this step include the IC Compiler and Custom Designer families of products.

Resolution enhancement (step 228): This step involves geometric manipulations of the layout to improve manufacturability of the design. Example EDA software products from Synopsys, Inc. that can be used at this step include Proteus, ProteusAF, and PSMGen products.

Mask data preparation (step 230): This step provides mask-making-ready "tape-out" data for production of masks for lithographic use to produce finished chips. Example EDA software products from Synopsys, Inc. that can be used at this step include the CATS® family of products.

Parallel flow. The integrated circuit manufacturing flow includes a parallel flow, as follows:

(1) Develop individual process steps for manufacturing the integrated circuit. This can be modeled with EDA tools such as the Synopsys tools "Sentaurus Process", "Sentaurus Topography", and "Sentaurus Lithography". The input information here is the process conditions like temperature, reactor ambient, implant energy, etc. The output information is the change in geometry or doping profiles or stress distribution.

(2) Integrate the individual process steps into the complete process flow. This can be modeled with EDA tools such as the Synopsys tool "Sentaurus Process". The input information here is the collection of the process steps in the appropriate sequence. The output is the geometry, the doping profiles, and the stress distribution for the transistors and the space in between the transistors.

(3) Analyze performance of the transistor manufactured with this process flow. This can be done with EDA tools such as the Synopsys tool "Sentaurus Device". The input information here is the output of step (3) and the biases applied to transistor terminals. The output information is the currents and capacitances for each bias combination. For silicon based processes or structures, much of the information about the materials needed for simulation of electrical behavior using these tools is well known. For other materials, it may be necessary to generate or provide parameters like lattice structure, diffusivity and concentration of defects, and the like in order to support device and process scale simulations. An EDA tool for generating parameters like this is described herein.

(4) If necessary, modify the process steps and the process flow to achieve the desired transistor performance. This can be done iteratively by using tools such as the Synopsys tools mentioned above.

Once the process flow is ready, it can be used for manufacturing multiple circuit designs coming from different fabless companies. The EDA flow 212-230 will be used by such fabless companies. The parallel flow described here is used at a foundry to develop a process flow that can be used to manufacture designs coming from their fabless customers. A combination of the process flow and the masks 230 are used to manufacture any particular circuit. If the integrated circuit is manufactured at an IDM (integrated device manufacturer) company instead of the combination of a fables company and a foundry, then both parallel flows described above are done at the same IDM company.

There is also a bridge between these tools and the 212-230 EDA tools. The bridge can be an EDA tool a Synopsys tool "Seismos" that applies compact proximity models for particular circuit design and layout to obtain netlist with instance parameters for each individual transistor in the circuit as a function of its neighborhood and stress, including material conversion stress.

Incorporated by reference herein are the following documents, which provide additional information about terms and components referenced herein:

Mathieu Luisier, "Quantum Transport for Engineers Lecture 4: Wave Function (WF) formalism and electrostatics", Integrated Systems Laboratory, ETH Zurich (2012).

Kyoung-Youm Kim and Byoungho Lee, "Quantum transport modeling in anisotropic semiconductors using Wigner function formulation", Proceedings Conference on Optoelectronic and Microelectronic Materials and Devices, COMMAD 2000. (2000)

Daniel Arovas, "Lecture Notes on Condensed Matter Physics, Chapter 1 Boltzmann Transport", Department of Physics, University of California, San Diego (2010).

R. Grau-Crespo, "Electronic structure and magnetic coupling in FeSbO4: A DFT study using hybrid functionals and GGA+U methods", PHYSICAL REVIEW B 73, (2006).

Michel Côté, "Introduction to DFT+U", International Summer School on Numerical Methods for Correlated Systems in Condensed Matter, Université de Montréal.

A. Muramatsu, "Quantum Monte Carlo for lattice fermions", in: M. P. Nightingale, C. J. Umriga (Eds.), Proceedings of the NATO Advanced Study Institute on Quantum Monte Carlo Methods in Physics and Chemistry, Kluwer Academic Publishers, 1999.

E. K. U. Gross and N. T. Maitra, "Introduction to TDDFT", Chapter in Fundamentals of Time-Dependent Density Functional Theory, Springer-Verlag 2012.

M. A. L. Marques, E. K. U. Gross, Time-dependent density functional theory, in: C. Fiolhais, F. Nogueira, M. A. L. Marques (Eds.), A Primer in Density Functional Theory, Springer Lecture Notes in Physics, vol. 620, Springer 2003, pp. 144-184.

D. A. Ryndyk, "Tight-binding model", Lectures 2006-2007, Dresden University of Technology.

R. E. Bank, "Numerical Methods for Semiconductor Device Simulation", IEEE Transactions on Electron Devices, Vol. ED-30, No. 9, 1983.

J. F. Lee, "Time-Domain Finite-Element Methods", IEEE Transactions on Antenna and Propagation, Vol. 45, NO. 3, 1997.

R. Eymard, "Finite Volume Methods", course at the University of Wroclaw, 2008.

X. L. Chen, "An advanced 3D boundary element method for characterizations of composite materials", Engineering Analysis with Boundary Elements 29, 513-523 (2005).

D. Marx, "Ab initio molecular dynamics: Theory and Implementation", Modern Methods and Algorithms of Quantum Chemistry, J. Grotendorst (Ed.), John von Neumann Institute for Computing, Julich, NIC Series, Vol. 1, 2000.

BURKE, K., et al., "The ABC of DFT" (2007), which among other things describes DFT.

KRESSE, G., et. al., VASP the Guide (Sep. 9, 2013).

The invention claimed is:

1. A computer-implemented method comprising:
   causing an ab initio simulation module to perform an environmentally-adapted ab initio simulation for each of a plurality of specified environments by extracting physical quantities of semiconductor materials;

causing an intermediate module to produce ab initio simulation outputs for each of the specified environments in dependence upon the ab initio simulations; and processing, by the intermediate module, each of the ab initio simulation outputs to generate higher scale simulation module inputs corresponding to the respective specified environment, wherein the higher scale simulation module inputs include a set of the physical quantities of the semiconductor materials extracted by the ab initio simulation module.

2. The computer-implemented method of claim 1, wherein the set of the physical quantities of the semiconductor materials, for the respective specified environment, includes any of: non-parabolicity, bandgaps, effective mass tensor, and N-band k.p model parameters, where N is an integer.

3. The computer-implemented method of claim 1, wherein the ab initio simulation module includes one or more of the following: a density functional theory module, a quantum Monte Carlo module, a time dependent density functional theory module and an ab initio molecular dynamics module.

4. The computer-implemented method of claim 1, wherein the intermediate module includes a member of the group consisting of: a classical molecular dynamics module, a tight-binding module, and a non-equilibrium Green's function module.

5. The computer-implemented method of claim 1, further comprising a set of non-ab initio simulation modules receiving and processing the higher scale simulation module inputs that correspond to a particular one of the specified environments to perform EDA simulations including the particular specified environment.

6. The method of claim 1, wherein processing each of the ab initio simulation outputs into higher scale simulation module inputs corresponding to the respective specified environment comprises:

determining a discrepancy between the higher scale simulation module inputs and the ab initio simulation outputs for each of the specified environments; and iteratively executing the intermediate module to reduce the discrepancy between the higher scale simulation module inputs and the ab initio simulation outputs.

7. A system comprising:
a memory; and
a data processor coupled to the memory, the data processor configured to:

cause an ab initio simulation module to perform an environmentally-adapted ab initio simulation for each of a plurality of specified environments by extracting physical quantities of semiconductor materials;

cause an intermediate module to produce ab initio simulation outputs for each of the specified environments in dependence upon the ab initio simulations; and process, by the intermediate module, each of the ab initio simulation outputs to generate higher scale simulation module inputs corresponding to the respective specified environment, wherein the higher scale simulation module inputs include a set of the physical quantities of the semiconductor materials extracted by the ab initio simulation module.

8. The system of claim 7, wherein the set of the physical quantities of the semiconductor materials, for the respective specified environment, includes any of: non-parabolicity, bandgaps, effective mass tensor, and N-band k.p model parameters, where N is an integer.

9. The system of claim 7, wherein the ab initio simulation module includes one or more of the following: a density functional theory module, a quantum Monte Carlo module, a time dependent density functional theory module and an ab initio molecular dynamics module.

10. The system of claim 7, wherein the intermediate module includes a member of the group consisting of: a classical molecular dynamics module, a tight-binding module, and a non-equilibrium Green's function module.

11. The system of claim 7, further comprising a set of non-ab initio simulation modules receiving and processing the higher scale simulation module inputs that correspond to a particular one of the specified environments to perform EDA simulations including the particular specified environment.

12. The system of claim 7, wherein processing each of the ab initio simulation outputs into higher scale simulation module inputs corresponding to the respective specified environment comprises:

determining a discrepancy between the higher scale simulation module inputs and the ab initio simulation outputs for each of the specified environments; and iteratively executing the intermediate module to reduce the discrepancy between the higher scale simulation module inputs and the ab initio simulation outputs.

* * * * *